United States Patent [19]

Mushabac

[11] Patent Number: 5,545,039
[45] Date of Patent: Aug. 13, 1996

[54] METHOD AND APPARATUS FOR PREPARING TOOTH OR MODIFYING DENTAL RESTORATION

[76] Inventor: David R. Mushabac, 919 Ocean Ave., Brooklyn, N.Y. 11226

[21] Appl. No.: 694,444

[22] Filed: May 1, 1991

Related U.S. Application Data

[63] Continuation-in-part of Ser. No. 507,162, Apr. 10, 1990, and Ser. No. 613,354, Nov. 14, 1990, Pat. No. 5,448,472, which is a continuation-in-part of Ser. No. 507,162, Apr. 10, 1990.

[51] Int. Cl.$^6$ .................... A61C 5/00; A61C 5/08
[52] U.S. Cl. ........................... 433/215; 433/218
[58] Field of Search ............... 433/29, 214, 215, 433/218, 219, 223, 229, 72; 364/474.24, 474.25, 474.26, 474.27, 474.28, 474.33

[56] References Cited

U.S. PATENT DOCUMENTS

| | | | |
|---|---|---|---|
| 3,971,133 | 7/1976 | Mushabac | 32/2 |
| 4,182,312 | 1/1980 | Mushabac | 433/68 |
| 4,184,175 | 1/1980 | Mullane, Jr. | 433/215 X |
| 4,239,431 | 12/1980 | Davini | 414/1 |
| 4,349,277 | 9/1982 | Mundy et al. | 356/376 |
| 4,431,420 | 2/1984 | Adair | 433/199 |
| 4,436,684 | 3/1984 | White . | |
| 4,478,580 | 10/1984 | Barrut | 433/223 |
| 4,525,858 | 6/1985 | Cline et al. | 382/1 |
| 4,564,295 | 1/1986 | Halioua | 356/376 |
| 4,575,805 | 3/1986 | Moermann et al. | 364/474 |
| 4,577,968 | 3/1986 | Makosch | 356/356 |
| 4,611,288 | 9/1986 | Duret et al. . | |
| 4,657,394 | 4/1987 | Halioua | 356/376 |
| 4,663,720 | 5/1987 | Duret et al. . | |
| 4,742,464 | 5/1988 | Duret et al. | 364/474 |
| 4,763,791 | 8/1988 | Halverson et al. . | |
| 4,764,877 | 8/1988 | Tanaka et al. | 364/474.33 |
| 4,791,940 | 12/1988 | Hirschfeld et al. | 433/72 X |
| 4,837,732 | 6/1989 | Brandestini et al. . | |
| 4,879,664 | 11/1989 | Suyama et al. | 364/474.28 |
| 4,936,862 | 6/1990 | Walker et al. . | |
| 4,941,826 | 7/1990 | Loran et al. . | |
| 5,022,856 | 6/1991 | Zimble | 433/72 |
| 5,027,281 | 6/1991 | Rekow et al. | 364/474.24 |
| 5,067,086 | 11/1991 | Yamazaki et al. | 364/474.03 X |
| 5,092,022 | 3/1992 | Duret | 433/25 X |
| 5,178,536 | 1/1993 | Werly et al. | 433/29 |
| 5,320,462 | 6/1994 | Johansson et al. | 433/223 X |
| 5,369,490 | 11/1994 | Kawai et al. | 433/29 X |

OTHER PUBLICATIONS

Boone, P. M., Optical Methods to Measure Shape and Size, 10/87
Boone, P. M. Optical Methods to Measure Shape and Size, University of Gent

*Primary Examiner*—Nicholas D. Lucchesi
*Attorney, Agent, or Firm*—R. Neil Sudol; Henry D. Coleman

[57] ABSTRACT

A tooth preparation or dental restoration modification apparatus comprises a material removal device for removing material from an object such as a tooth or dental restoration form, a guide element operatively connected to the material removal device for enabling a guiding of the material removal device under the control of an operator, and a light projector for projecting a visible point of light onto a predetermined location on the object, thereby serving as an indicator to the operator that material is to be removed from the object at the location.

13 Claims, 16 Drawing Sheets

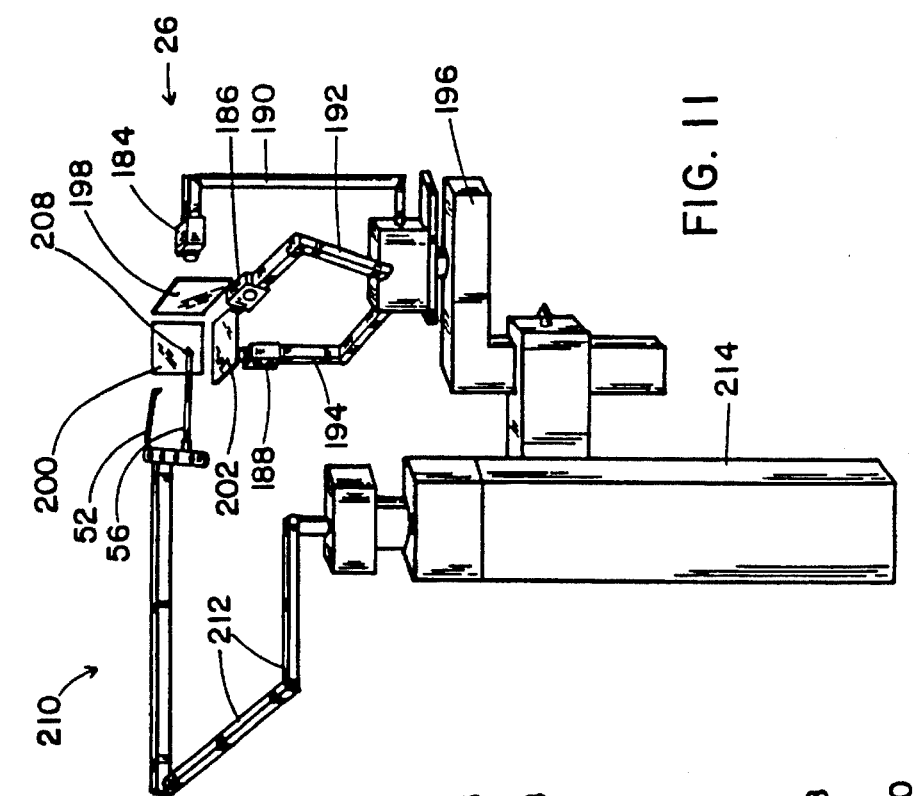
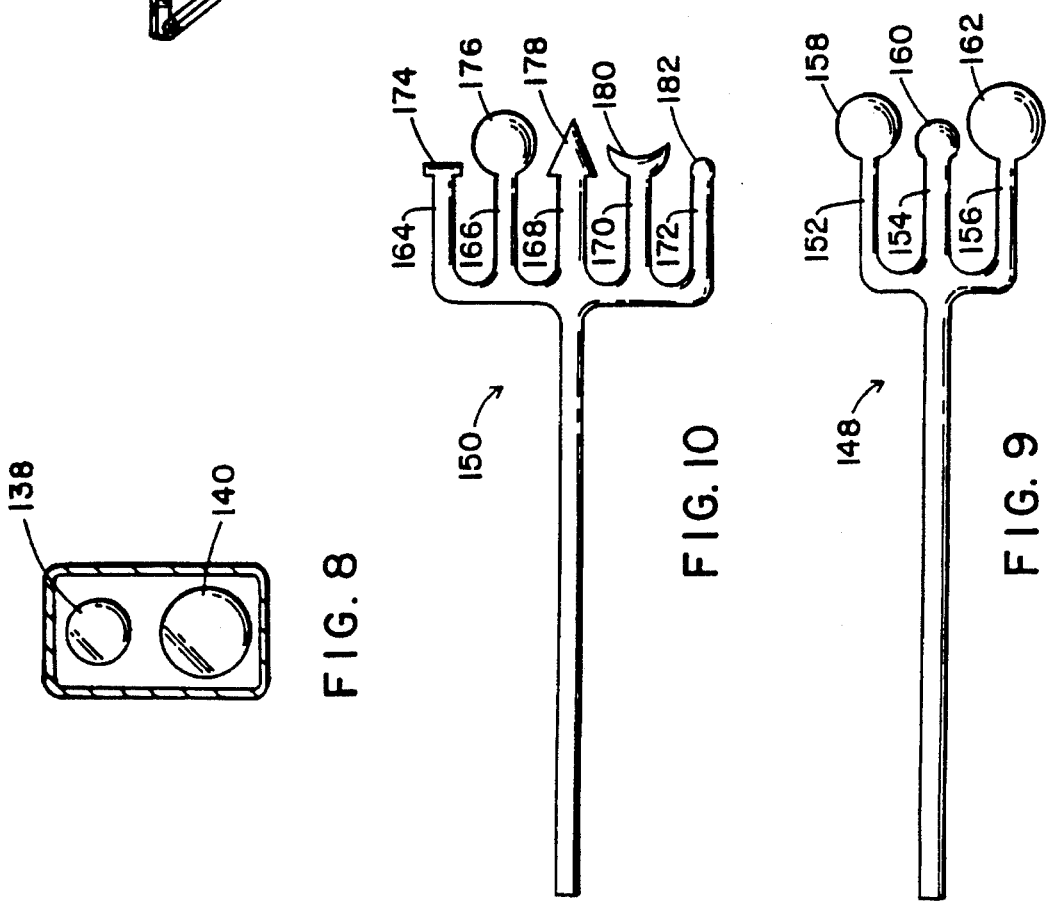

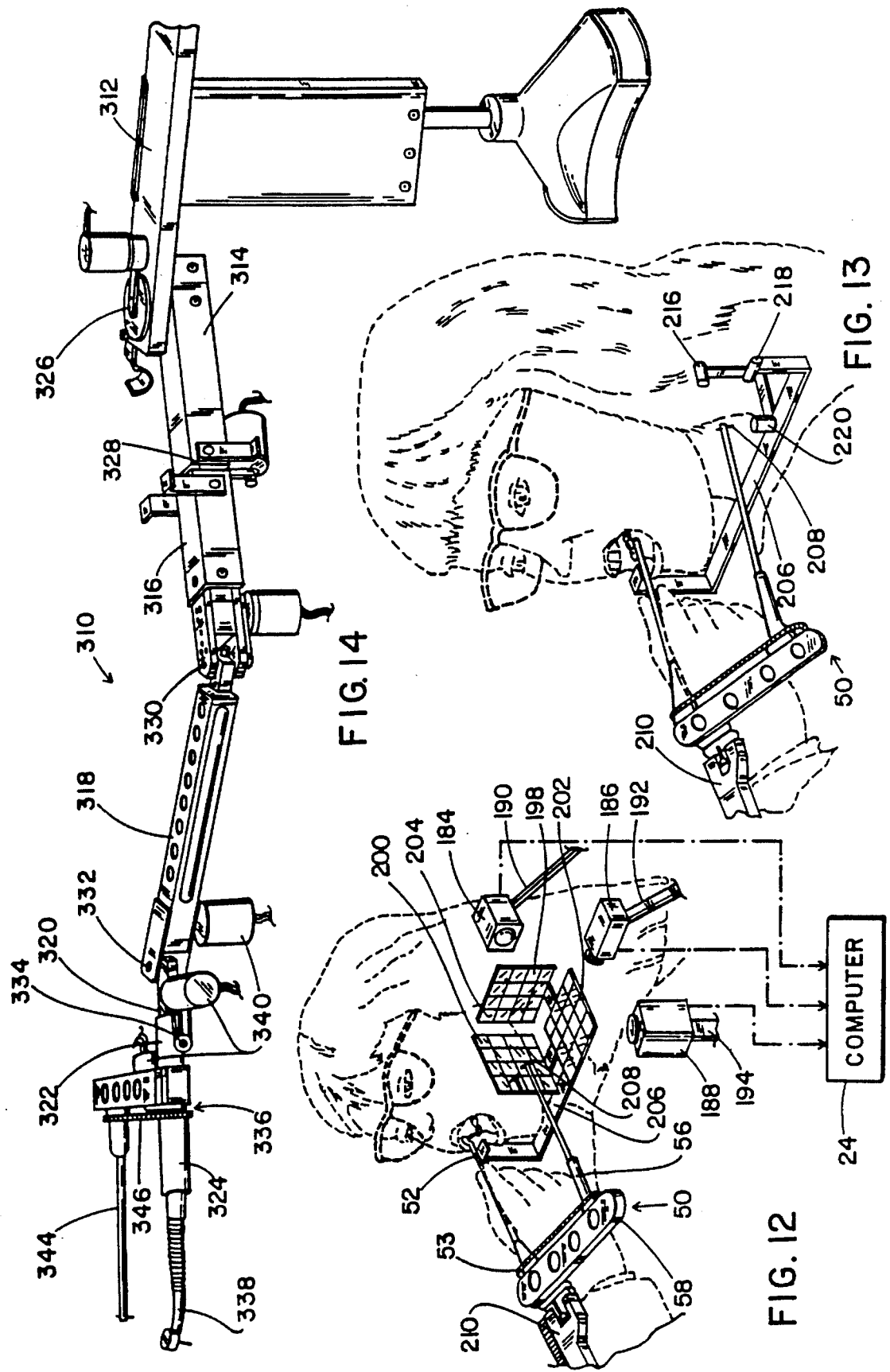

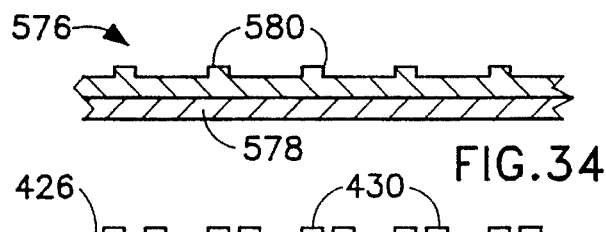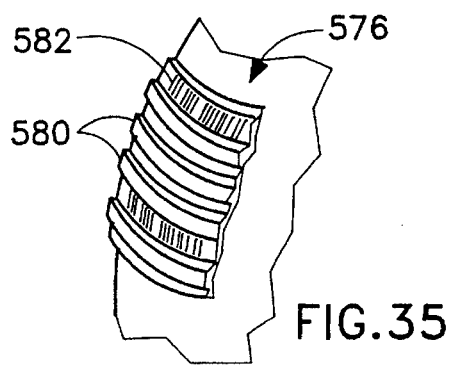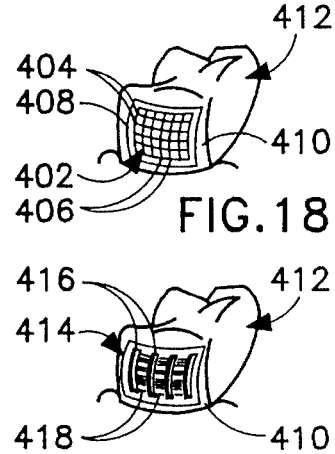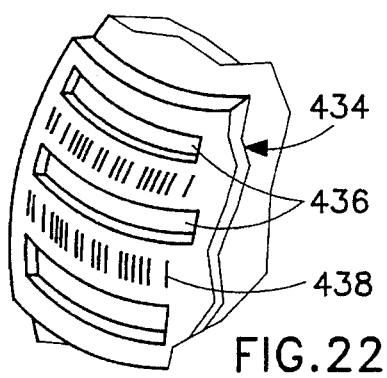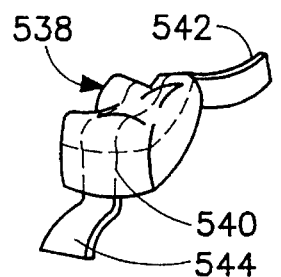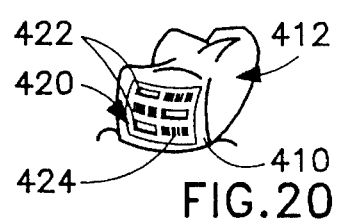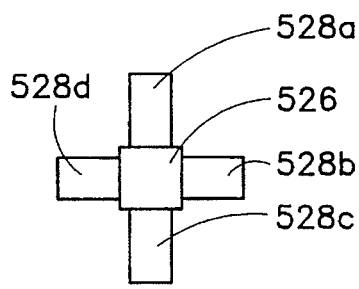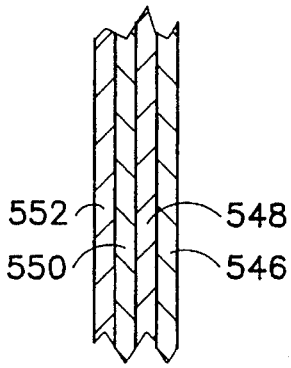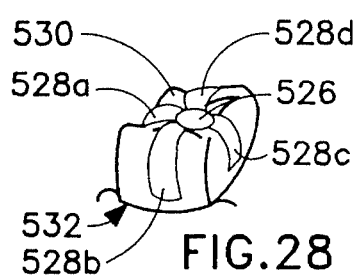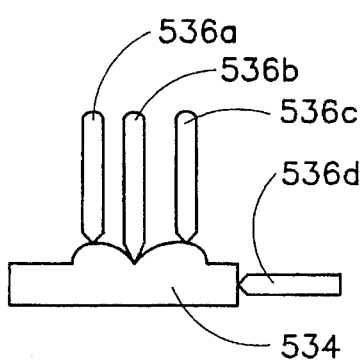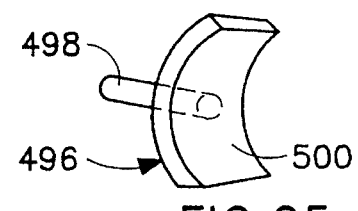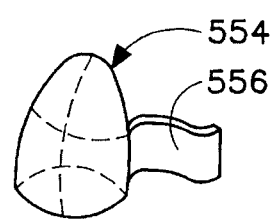

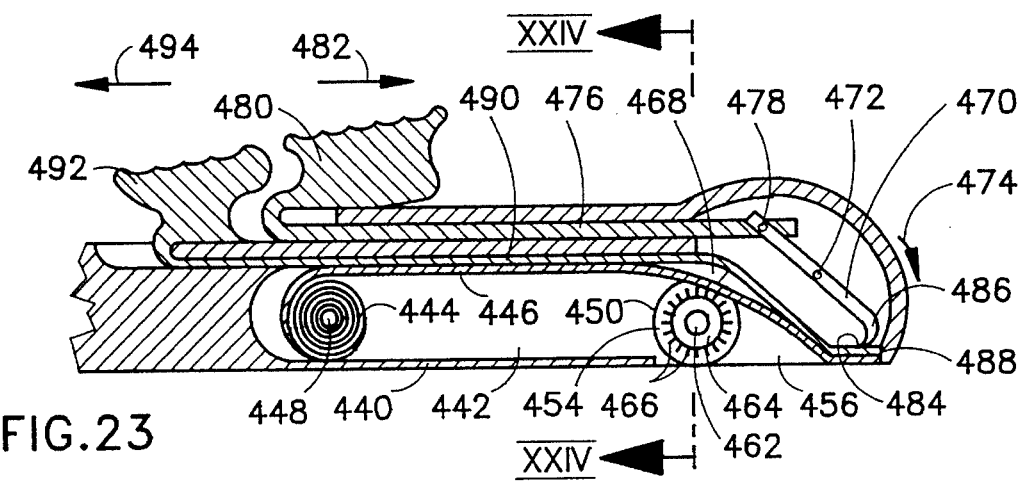
FIG. 23
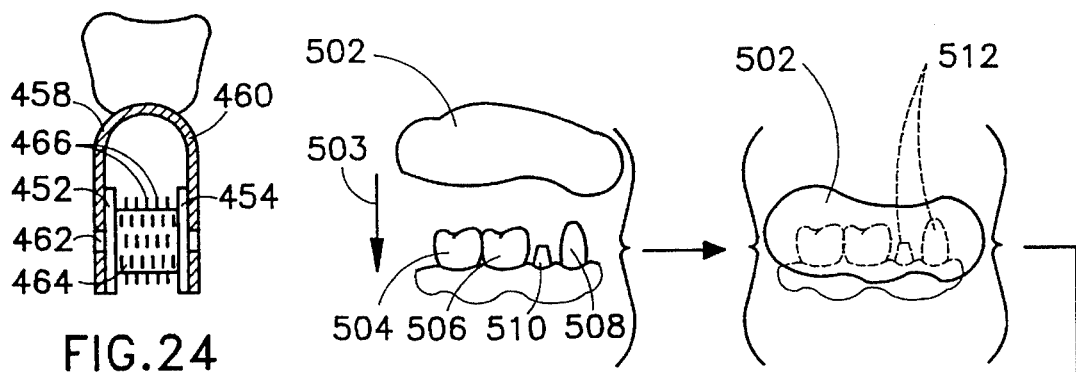
FIG. 24
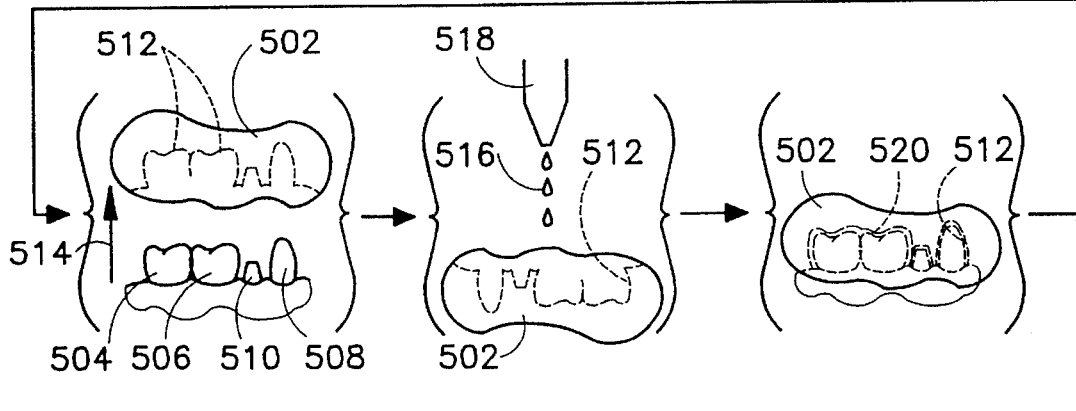
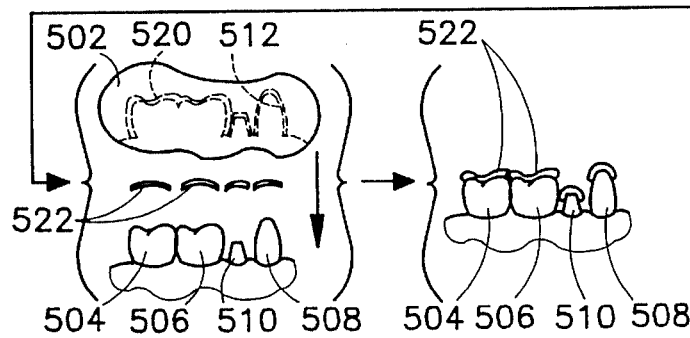
FIG. 26

METHOD AND APPARATUS FOR PREPARING TOOTH OR MODIFYING DENTAL RESTORATION

CROSS-REFERENCE TO A RELATED APPLICATION

This application is a continuation-in-part of commonly owned application Ser. No. 507,162 filed Apr. 10, 1990 now pending. In addition, this application is a continuation-in-part of commonly owned application Ser. No. 613,354 filed Nov. 14, 1990 now U.S. Pat. No. 5,448,492 as a continuation-in-part of Ser. No. 507,162 filed Apr. 10, 1990, pending.

BACKGROUND OF THE INVENTION

This invention relates to a device for use in preparing a tooth for receiving a restoration or prosthetic dental appliance such as a filling or crown. Such a device may also be used to modify a dental restoration or appliance, for example, prior to insertion or attachment of the restoration in a patient's mouth. This invention also relates to an associated method for preparing a tooth or modifying a dental restoration. This invention also concerns a dental diagnostic apparatus which facilitates the loading and processing of digitized dental data by a computer.

In prior pending application Ser. No. 507,162, a system is disclosed for gathering digitzed data pertaining to a patient's dentition. More particularly, the digitized data represents contours and surfaces of the patient's teeth. A computer which receives the digitized data is then operated to assist the dental practitioner in selecting a dental prosthesis or restoration from a kit of preformed restorations. The computer also assists the dental practitioner in preparing one or more teeth for receiving a dental restoration.

It is probable that a dental practitioner will wish to modify a dental preform to conform to an actual tooth preparation which the dentist has preferred over a preparation recommended the computer in accordance with a preprogrammed hierarchy.

OBJECTS OF THE INVENTION

An object of the present invention is to provide a method and apparatus to assist a dental practitioner or lab technician in preparing a tooth or in moddifying a dental restoration or prosthesis.

Another object of the present invention is to provide such a method and apparatus which varies only by a small differential from existing dental practice.

Another, more particular, object of the present invention is to provide such a method and apparatus wherein machining, grinding or polishing operations are performed by hand by the dental practitioner, with an automatically implemented guide.

Yet another object of the present invention is to provide an improved apparatus and method for informing a computer as to particulars of incoming digitized tooth data.

SUMMARY OF THE INVENTION

A tooth preparation or dental restoration modification apparatus comprises, in accordance with the present invention, a material removal device for removing material from an object such as a tooth or dental restoration form, a guide element operatively connected to the material removal device for enabling a guiding of the material removal device under the control of an operator, and a light projector for projecting a visible point of light onto a predetermined location on the object, thereby serving as an indicator to the operator that material is to be removed from the object at the location.

In accordance with another feature of the invention, the tooth preparation or dental restoration modification apparatus further comprises a control unit for determining points of excess material on the object and a communication device separate from the light projector and operatively connected to the control unit for instructing the operator as to locations of points of excess material on the object. Specifically, the communication device includes a display for presenting visually detectable information. More specifically, the communication device further includes circuitry for showing an image of the object on the display.

In accordance with another feature of the invention, the tooth preparation or dental restoration modification apparatus further comprises a data input device operatively connected to the control unit for providing the control unit with electrically encoded data specifying at least surface contours of the object, whereby the control unit is provided with information for generating the image. In particular, the data input device includes a scanner for optically scanning a surface of the object and transmitting a video signal of the surface to the computer. More particularly, the data input device also includes a manipulable stylus-type instrument having a distal tip engageable with the object and further includes a position detector for monitoring the location of the instrument tip relative to the object and for feeding electrically encoded data regarding the tip location to the control unit.

Pursuant to another feature of the present invention, where the object is a tooth inside the mouth of a patient, the communication device includes a simulation or model of the tooth and includes a structure for supporting the simulation outside the mouth of the patient. The communication device further includes an additional light projector for projecting a visible point of light onto a predetermined point on the simulation corresponding to the predetermined location on the tooth.

In accordance with a supplemental feature of the invention, the tooth preparation or dental restoration modification apparatus includes a monitoring device operatively connected to the guide element for monitoring the position thereof. The tooth preparation or dental restoration modification apparatus also includes means operatively coupled to the monitoring device and the principal light projector for inducing that projector to terminate projection of the visible point of light upon attainment of a predetermined position by the guide element. Alternatively, or additionally, circuitry is operatively coupled to the monitoring device and the light projector for inducing the light projector to initiate projection of the visible point of light upon attainment of a predetermined position by the guide element.

Pursuant to a specific feature of the present invention, the light projector is attached to the guide element.

Pursuant to another specific feature of the present invention, the light projector includes an optical element and a mechanical device operatively connected to the optical element for moving at least a portion of the optical element to change a direction of a light beam transmitted through the optical element. The optical element may take the form of an optical fiber. Alternatively, the optical element may take the form of a lens, prism or mirror.

Pursuant to a different specific feature of the present invention, the light projector includes a bundle of optical fibers and a selective light transmission device for transmitting a light beam through a selected one of the fibers.

A method for preparing a tooth or modifying a dental restoration comprises, in accordance with the present invention, the steps of (a) projecting a visible point of light onto a predetermined location on an object such as a tooth or dental restoration, thereby serving as an indicator to an operator that material is to be removed from the object at that location, (b) guiding a material removal device to the predetermined location, upon projection of the visible point of light onto the location, and (c) operating the material removal device to remove material from the object at the predetermined location.

Further steps in accordance with the present invention include at least partially automatically determining points of excess material on the object and, in a step separate and distinct from the step of projecting, at least partially automatically instructing the operator as to locations of points of excess material on the object. The step of instructing advantageously includes the step of displaying visually detectable information. More particularly, the step of instructing further includes the step of displaying an image of the object on a display.

Pursuant to another feature of the present invention, the method further comprises the step of generating electrically encoded data specifying at least surface contours of the object, thereby providing a control unit with information for automatically generating the image. The step of generating may include the step of optically scanning a surface of the object and transmitting a video signal of the surface to a computer. Alternatively or additionally, the step of generating includes the step of monitoring the location of a tip of a manipulable stylus-type instrument relative to the object and feeding electrically encoded data regarding the location of the instrument tip to the computer.

Pursuant to another feature of the present invention, the method further comprises the step of monitoring the position of the material removal device relative to the object and also comprises the step of terminating projection of the visible point of light upon attainment of a predetermined position by the material removal device. Alternatively or additionally, the operation of the material removal device may be automatically terminated upon attainment of a predetermined position by the material removal device. Moreover, projection of the visible point of light may be initiated automatically upon attainment of a predetermined position by the material removal device.

A dental diagnostic apparatus comprises, in accordance with the present invention, a computer, a data input device operatively connected to the computer for providing the computer with electrically encoded data specifying surface contours of the object, and a voice-recognition device operatively connected to the computer for receiving and decoding a voice signal identifying the object or subfeatures within the object. A display is preferably connected to the computer for displaying a three-dimensional graphic representation of the object in response to signals generated by the computer in accordance with electrically encoded data from the data input device and verbal instructions received from an operator via the voice-recognition device.

BRIEF DESCRIPTION OF THE DRAWING

FIG. 8 is an elevational view of a distal end of the embodiment of FIG. 7, taken in the direction of arrow VIII.

FIG. 9 is a plan view of a reference stylus usable in conjunction with the data generating device of FIGS. 3 and 7.

FIG. 10 is a plan view of another reference stylus usable in conjunction with the data generating device of FIGS. 3 and 7.

FIG. 11 is a partially diagrammatic perspective view of an embodiment of a contour data generating device shown in FIG. 1.

FIG. 12 is a partial perspective view, on an enlarged scale, of the contour generating device of FIG. 11, showing its use with a dental patient.

FIG. 13 is a partial perspective view, on an even larger scale, of another embodiment of the contour generating device of FIG. 1, showing its use with a dental patient.

FIG. 14 is a perspective view of another contour data generating device usable in a dentistry system.

FIG. 18 is a schematic perspective view of a tooth to which a reference marking strip has been applied.

FIG. 19 is a schematic perspective view of the tooth of FIG. 18, with a different reference marking strip.

FIG. 20 is a schematic perspective view of the tooth of FIGS. 18 and 19, with another reference marking strip.

FIG. 21 is a longitudinal cross-sectional view of another reference marking strip.

FIG. 22 is a partial perspective view, on an enlarged scale, of yet a further reference marking applicator strip, showing the strip applied to a tooth surface.

FIG. 23 is a longitudinal cross-section view of a marking tape applicator device.

FIG. 24 is a transverse cross-sectional view taken along line XXIV—XXIV in FIG. 23.

FIG. 25 is a perspective view of a marking tape applicator element.

FIG. 26 is a diagrammatic flow chart representing successive steps in the attachment of reference marker tape strips to tooth surfaces.

FIG. 27 is a top elevational view of an applicator member for facilitating the provision of distance reference marks and/or identification markings at a mouth surface.

FIG. 28 is a perspective view showing use of the applicator member of FIG. 27 on a tooth.

FIG. 29 is a top elevational view of another applicator member for facilitating the provision of distance reference marks and/or identification markings at a mouth surface.

FIG. 30 is a perspective view of device for applying reference markers to the surface of a tooth.

FIG. 31 is a cross-sectional view of a wall of the device of FIG. 30.

FIG. 32 is a perspective view of a similar device for applying reference markers to the surface of a prepared tooth.

FIG. 34 is a cross-sectional view of a tape strip for facilitating tracing of a tooth contour.

FIG. 35 is a partial perspective view, on an enlarged scale, of the tape strip of FIG. 34 attached to a tooth surface.

DETAILED DESCRIPTION OF THE INVENTION

Figure 1:
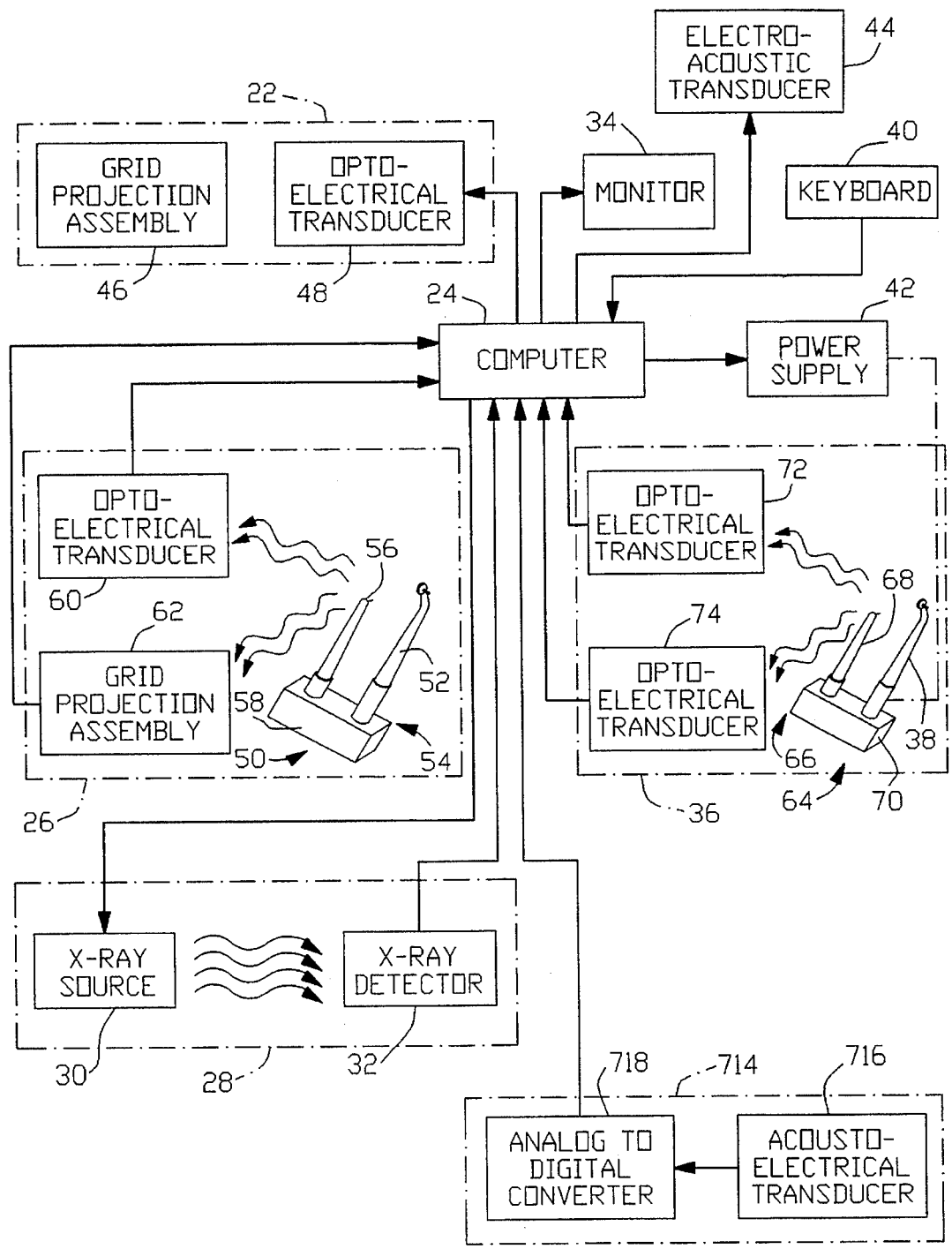
FIG. 1 is a block diagram of a system effecting a desired modification in the shape of a pre-existing object such as a tooth to which access is restricted.

As illustrated in FIG. 1, a computerized interactive system for producing a modification in the shape of an object such as a tooth to which access is limited comprises a first data generating device or assembly 22 for providing a computer 24 with electrically encoded data, specifically, digitized video signals representing a contoured surface of an object such as a tooth. A second data generating device or assembly 26 is operatively connected to computer 24 for transmitting thereto digitized signals containing information pertaining to a curvilinear contour on the surface of the contoured surface of the tooth. In addition, computer 24 may receive from a third data generating device or assembly 28 digitized input signals relating to internal structures of the tooth being scanned. Specifically, data generating device 28 may take the form of an X-ray device such as used in current intra-oral radiology or other methodologies and basically comprises a source 30 of X-ray radiation and a detector 32 for receiving the X-ray radiation after it passes through a tooth and converting the incident radiation into a digital data stream fed to computer 24.

As further illustrated in FIG. 1, the computerized interactive dentistry system also comprises a display device 34 such as a monitor or holographic projector. In response to data signals, computer 24 generates a three-dimensional view on display of monitor 34 of the tooth or teeth under examination. More specifically, computer 24 is provided with any commercially available stereophotogrammetric triangulation program for calculating and displaying, on the basis of the video input signals from data generating devices 22, 26 and 28, three dimensional surfaces and contours of the tooth or teeth.

The computerized interactive dentistry system of FIG. 1 further includes another data generating device or assembly 36 which provides computer 24 with digitized video information as to the location of the operative tip of a cutting instrument 38 such as a dentist's drill relative to the three-dimensional structural features of the tooth. Data generating device 36 thus enables computer 24 to monitor modifications to the shape of the tooth as those modification are being made in the tooth.

The system of FIG. 1 is further provided with any of several instruction input devices such as a keyboard 40, a mouse (not shown), or a contact sensitive surface of monitor 34, whereby an operator such as a dentist or dental technician may instruct the computer to display a desired tooth preparation on monitor 34. In addition, or alternatively, computer 24 may use input from drill data generating device 36 as instructions regarding, for example, the depth of a tooth preparation to be displayed on monitor 34.

Upon selecting a desired tooth preparation illustrated on monitor 34, the dentist operates drill 38 to cut a recess into the tooth (in the case of a filling or inlay) or to remove an outer layer of the tooth (in the case of preparing a form/shape for a crown or other prosthetic restoration). Computer 24 monitors the location of the operating tip of the drill via data generating device 36 and, if the drill approaches a boundary previously defined to the computer during an interactive tooth preparation selection operation, either interrupts the power provided to the drill via a supply 42 or alerts the dentist via a signaling device such as an electro-acoustic transducer 44.

As depicted schematically in FIG. 1 and discussed in greater detail hereinafter, data generating device 22 includes a grid projection assembly 46 for optically imposing a grid onto the surface of the patient's tooth. Data generating device 22 also includes an opto-electrical transducer 48 such as a charge-coupled device for optically sensing or scanning the tooth surface onto which the grid is projected by assembly 46. It is to be understood that the grid pattern projected on the tooth surface need not be an orthogonal grid having two sets of lines at right angles to one another, but may instead have the two sets of lines oriented at an acute angle. Moreover, although preferred embodiments incorporate an optical grid, it is also contemplated that a grid may be imposed onto the tooth surface by other methods, such as adhesively attaching to the tooth surface a transparency provided with a grid.

As further depicted in FIG. 1 and described in detail hereinafter, data generating device 26 comprises a pantograph-type component 50 which incorporates a stylus member 52 and a pantograph extension 54 in turn including a pantograph arm 56 and a bridge element 58. Bridge element 58 connects pantograph arm 56 to stylus member 52. Data generating device 26 further comprises at least a pair of opto-electrical transducers 60 and 62 preferably in the form of respective charge-coupled devices ("CCD"s). Pantograph component 50 enables computer 24 to track, from outside the mouth, the motions of the tip of the stylus member inside the mouth and even beneath the gum line.

Accordingly, data generating devices 22, 26 and 28 provide to computer 22 electrically encoded data completely defining the structure of the tooth on which a dentist is working. Computer 24 then "draws" the tooth on monitor 34. At that juncture the dentist instructs the computer to modify the displayed three-dimensional shape. For example, the dentist may use keyboard 40 to input a command that a predefined tooth preparation, in graphic form, be overlaid on the three-dimensional graphic representation of the tooth. The size of the tooth preparation relative to the tooth may be specified by entering a depth dimension via keyboard 40, data generating device 36, a mouse or a contact-sensitive surface of monitor 34. Alternatively, computer 24 may be programmed to automatically select a possible tooth preparation in accordance with the data from data generating devices 22, 26 and 28. In accordance with yet another alternative procedure, the dentist may command the computer to alter the graphic representation of the tooth, for example, by removing a layer of several millimeters from a surface selected by the dentist or by removing a selected volume of tooth from all five surfaces above the gum line to a contour below the gum line defined by the second data generating device 26.

As further depicted in FIG. 1 and described in detail hereinafter, data generating device 36 comprises a pantograph-type component 64 which incorporates drill 38 and a pantograph extension 66 in turn including a pantograph arm 68 and a bridge element 70. Bridge element 70 connects pantograph arm 68 to drill 38. Data generating device 36 further comprises at least a pair of opto-electrical transducers 72 and 74 preferably in the form of respective charge-coupled devices ("CCD"s). Pantograph component 64 enables computer 24 to track, from outside the mouth, the motions of the tip of drill 38 inside the mouth and even inside a tooth.

Data generating device 36 may be the same as data generating device 26 with stylus element 52 replaced by drill 38. Moreover, upon the selection of a desired tooth preparation via computer 24, monitor 34 and an instruction input device such as keyboard 40, drill 38 is used by the dentist to provide the displayed tooth preparation in the subject tooth. Computer 24 monitors the output signals of opto-electrical transducers 72 and 74 thereby tracks the cutting motions of the operating tip of drill 38 inside the subject tooth. The excavations into the tooth are displayed in real time on monitor 34 by computer 24.

Figure 2:
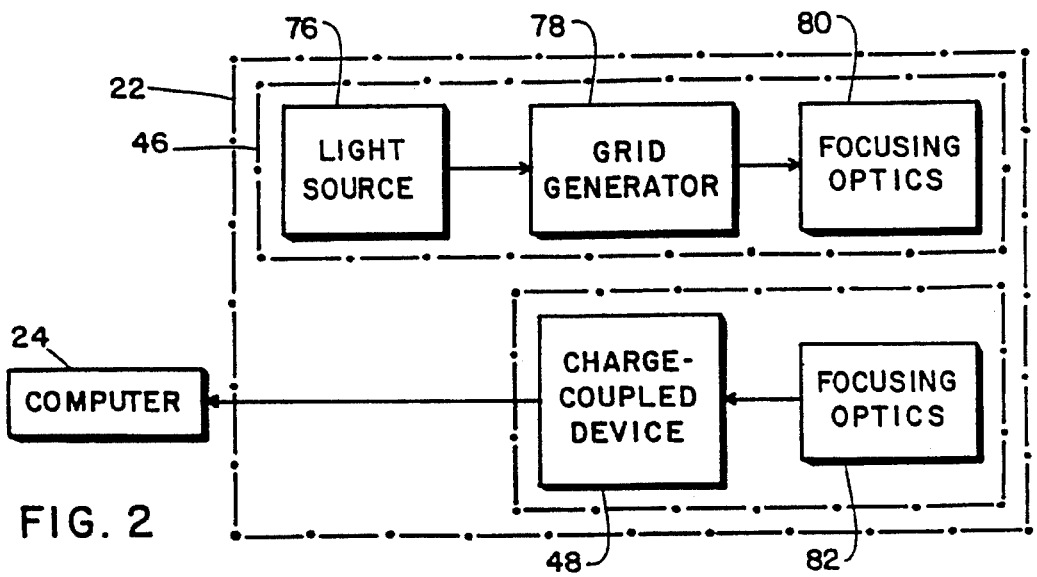
FIG. 2 is a block diagram showing details of a surface data generating device shown in FIG. 1.

As shown in FIG. 2, grid projection assembly 46 of data generating device 22 includes a light source 76, a grid generator 78 and an assembly 80 of light guides and lenses for guiding the grid light along a path through the data generating device and for focusing the grid light on the surface of a subject tooth. The light subsequently reflected from the tooth surface is gathered by further optical elements 82 and focused by those elements on the light sensitive sensor surface of charge-coupled device ("CCD") 48. In response to a sensed pattern of light intensities, CCD 48 generates and transmits to computer 24 a digitized video signal containing information used by computer to calculate the dimensions of the subject tooth and to display the tooth's structure in a three-dimensional graphic representation on monitor 34.

Figure 3:
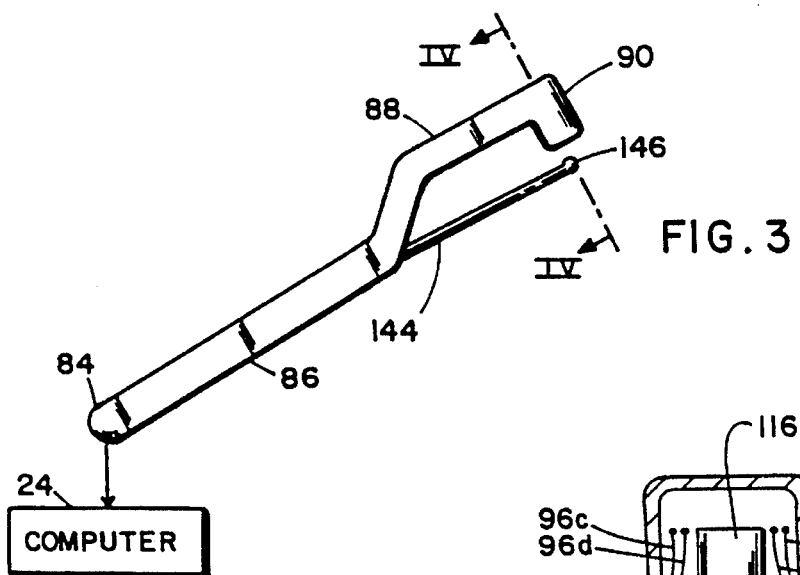
FIG. 3 is partially a block diagram and partially a schematic elevational view of a particular embodiment of the surface data generating device of FIG. 2.

As shown in FIG. 3, the components 76, 78, 80, 82 and 48 of data generating device 22 may be housed in an elongate instrument frame or holder 84 including a handle 86 and a stem portion 88 displaced laterally with respect to a longitudinal axis of handle 86.

Figure 4:
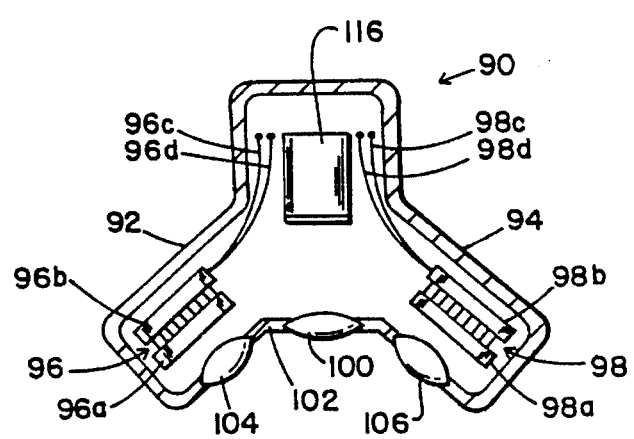
FIG. 4 is a cross-sectional view taken along line IV—IV in FIG. 3.

In a preferred form of the grid projection instrument, illustrated in detail in FIG. 4, holder 84 of FIG. 3 further includes a Y-shaped distal end portion 90 having a pair of hollow legs 92 and 94 housing respective CCDs 96 and 98. Each CCD includes a respective photosensitve sensor array 96a and 98b and respective sequencing and processing electronics 96b and 98b. The sequencing and processing electronics 96b and 98b have input and output leads 96c, 96d and 98c, 98d extending to computer 24 through stem portion 88.

Light containing a grid pattern is projected from Y-shaped distal end portion 90 through a focusing lens 100 mounted in a wall 102 between legs 92 and 94. The light subsequently reflected from a subject tooth is focused on sensor arrays 96a and 98a by a pair of lenses 104 and 106 disposed in legs 92 and 94. Lenses 104 and 106 may be considered parts of focusing optics 82 (FIG. 2), while lens 100 is part of focusing optics assembly 80.

Figure 5:
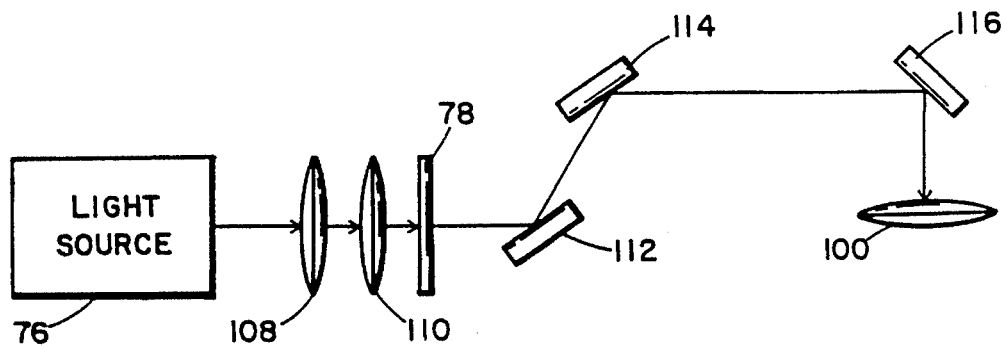
FIG. 5 is a detailed schematic diagram of optical components in a grid projection assembly included in the surface data generating device of FIG. 3.

As shown in detail in FIG. 5, grid projection assembly 46 includes light source 76 (also shown in FIG. 2), a pair of collimating lenses 108 and 110, grid generator 78 (see FIG. 2) in the form of a plate provided with a grid pattern, and three mirrors or prisms 112, 114, 116 for directing the grid-containing light rays through stem portion 88 (FIG. 3) to lens 100. Of course, frame or holder 84 may be provided with various movable mounting elements (not shown) for adjusting the focuses of the various lenses.

Figure 6:
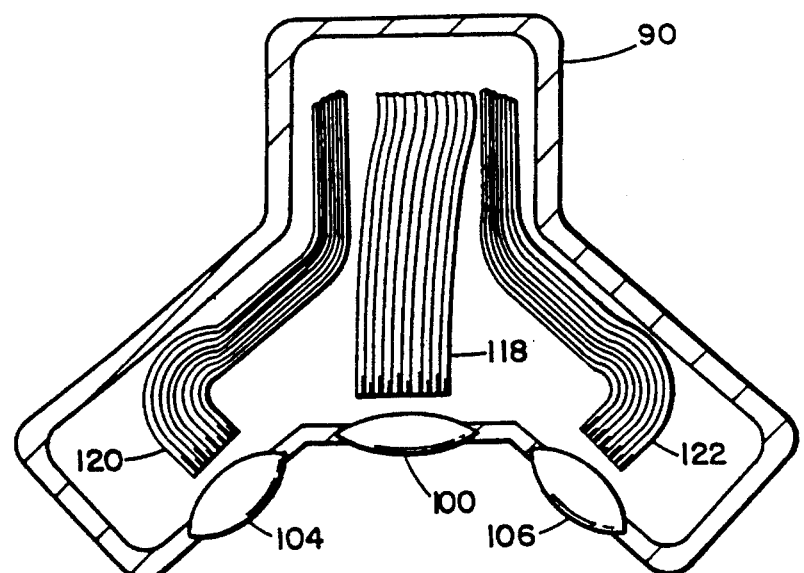
FIG. 6 is a cross-sectional view, similar to FIG. 4, of another particular embodiment of the surface data generating device of FIG. 2.

It is within the contemplation of the invention that the grid light may be guided through the grid projection instrument or frame 84 by elements other than those illustrated in FIG. 5. As depicted in FIG. 6, an output array of light beams is guided to lens 100 by a bundle 118 of optical fibers, while a pair of optical fiber input bundles 120 and 122 receive incoming optical radiation focused on the input ends of bundles by lenses 104 and 108.

Fiber bundles 120 and 122 guide the incoming radiation to a pair of CCDs (not shown) disposed in instrument frame 90 at a more proximal end of the frame, for example, in the handle. Rather than two separate CCDs, the first data generating device 22 may include a single CCD (not shown) disposed in the handle 84 (FIG. 3) and means for directing light from two separate optical pathways to the CCD.

Figure 7:
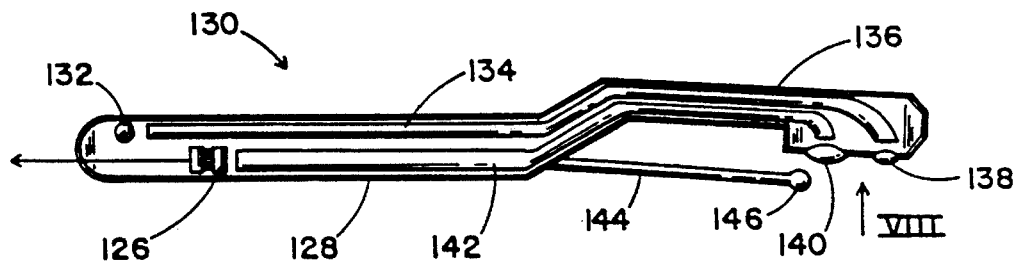
FIG. 7 is a schematic cross-sectional longitudinal view of yet another particular embodiment of the surface data generating device of FIG. 2.

As schematically shown in FIGS. 7 and 8, a data generating device or optical probe 124 may incorporate a single CCD transducer 126 disposed in a handle 128 of an elongate instrument frame or casing 130. The handle 128 also houses a grid source 132. An optical fiber bundle 134 guides a grid pattern from grid source 132 through a part of handle 128 and a stem portion 136 of frame 130 to a distal end of the probe. At the distal end, the grid pattern is focused by a lens 138 onto a subject tooth, the reflected radiation pattern being focused by another lens 140 onto the distal or input end of another fiber optic bundle 142 extending to CCD 126.

As shown in FIGS. 3 and 7, frame member 84 and optical probe frame 130 are provided with a stylus element 144 having an enlargement 146 at its distal end. Enlargement 146 is disposable in the visual field of the respective optical scanning element or elements, whether CCD 48, CCDs 96 and 98, or CCD 126, for providing computer 24 with a reference distance or dimension at the surface of a subject tooth being scanned. Computer 24 is thereby able to calculate absolute values for the dimensions of various surface features. Computer 24 measures distances by calculating the number of pixels in the respective sensor array (e.g., 96a and 98a) which cover a feature whose dimensions are being determined. Inasmuch as computer 24 is preloaded with the actual dimensions of enlargement 146, the computer is able to compute actual distances by comparing the number of pixels correpsonding to enlargement 146 with the number of pixels corresponding to the features of the tooth.

Stylus element 144 is retractable into handle 86 or 128. Retraction may be implemented either manually or automatically, for example, by a small motor and rack and pinion (not illustrated) inside the respective handle. Moreover, stylus 144 is advantageously replaceable by other elements such as stylus 148 shown in FIG. 9 or stylus 150 shown in FIG. 10.

Stylus 148 is formed at a distal end with three prongs 152, 154 and 156 each having a respective sphere 158, 160 and 162 at its free end. Spheres 158, 160 and 162 may have different sizes for facilitating the measurement of anatomical distances by computer 24. Similarly, stylus 150 has a plurality of prongs 164, 166, 168, 170 and 172 each provided at its free end with an enlarged formation 174, 176, 178, 180 and 182 of a respective geometric shape and a respective transverse dimension.

In using a data generating device equipped with stylus 148, a dentist places at least two of spheres 158, 160 and 162 on the surface of the tooth. Similarly, two enlarged end formations 174, 176, 178, 180 and 182 are positioned in engagement with a tooth surface during use of a data generating device incorporating stylus 150.

As depicted in FIGS. 11 and 12, contour data generating device 26 (FIG. 1) comprises, in a preferred embodiment, three CCD cameras 184, 186 and 188 fixed to the free ends of respective adjustable mounting arms 190, 192 and 194 in turn connected at their other ends to a pedestal member 196. Contour data generating device 26 further comprises three transparent plates 198, 200 and 202 each provided with a respective grid 204 (only one designated in the drawing) and secured to a common substantially L-shaped support arm 206. Support arm 206 is cemented or otherwise attached to the jaw of a patient P prior to the use of the contour data generating device.

It is to be noted that although plates 198, 200 and 202 are illustrated as being orthogonally disposed and as having Cartesian orthogonal grids, it is not necessary for effective calculation of distances and angles that the plates and grids be so oriented. An ordinary modification of the stereophotogrammetric triangulation program is all that is required for the system of FIG. 1 to function with plates 198, 200 and 202 and/or the grid lines thereof oriented at acute angles.

Any two CCD cameras 184, 186 and 188 correspond to opto-electrical transducers 60 and 62 of FIG. 1. Although three CCD cameras are preferred, in some instances two may be sufficient.

As further illustrated in FIGS. 11 and 12, contour data generating device 26 includes pantograph-type component 50. As described hereinabove with reference to FIG. 1 (includes essentially a mirror image of illustrations in FIG. 11 and 12), pantograph component 50 incorporates stylus member 52, pantograph arm 56 and bridge element 58. CCD Cameras 184, 186 and 188 enable computer 24 to track orthogonal components of the motion of a predetermined point 208 on pantograph arm 56 against respective reference frame plates 198, 200 and 200, respectively. Because pantograph arm 56 is fixed with respect to stylus member 52, computer 24 is accordingly able to track, from outside the mouth of patient P, the motions of the tip of the stylus member 52 inside the mouth and even beneath the gum line.

Pantograph component 50 is mounted to the free end of a linkage 210 including a plurality of pivotably interconnected arm members 212. The base of linkage 210, like pedestal member 196 is secured to a base 214.

Both stylus member 52 and pantograph arm 56 are rotatably secured to bridge element 58 so that they can rotate about respective longitudinal axes. Pantograph arm 56 is coupled to stylus member 52 via an endless toothed belt 53 whereby rotation of stylus arm 52 about its longitudinal axis by an operator results in a simultaneous rotary motion of pantograph arm 56.

Accordingly, stylus member 52 is free to be moved by an operator along three translational axes and three rotational axes, the resulting motion being duplicated by pantograph arm 56.

An alternative way for providing computer 24 with a reference frame against which to measure motions of pantograph arm 56 and concomitantly stylus member 52 is illustrated in FIG. 13. In the specific embodiment shown in FIG. 13, three CCD cameras 216, 218 and 220 are fastened to support member 206 in turn cementable, as discussed above, to the patient's jaw in which the subject tooth is rooted. Pursuant to this embodiment, no reference grids are necessary for computer 24 to monitor, via cameras 216, 218 and 220, the motion of pantograph arm 56 and thus stylus member 52.

It is to be noted that the camera assembly of FIG. 13 essentially includes three pixel arrays (not visible in the drawing) disposed in separate reference planes of a three dimensional coordinate system, with the casings of the cameras serving in part to hold three lenses (not designated with reference numerals) at pre-established distances with respect to the respective pixel arrays to focus the light from the tip 208 of the pantograph arm on the pixel arrays. The tip 208 of pantograph arm 56 may be provided with an LED or other marker element to facilitate detection by the optical scanning assembly comprising cameras 216, 218 and 220.

As illustrated in FIG. 14, contour data may be generated by an alternative technique employing a multiple segment support arm 310 which extends from a fixed platform 312. Support arm 310 includes segments 314, 316, 318, 320, 322 and 324 of which the first segment 314 is connected to platform 312. Segments 314–324 are pivotably connected to one another via six rotating joints 326, 328, 330, 332, 334 and 336. By incorporating six separate junctions for rotational movement, an operating instrument (e.g., drill) 338 connected to the free end of a last or outermost arm 324 can move with six degrees of freedom, specifically along three translational axes and three rotational axes.

Stationary platform 312 and segment 314 are connected at joint 326 to provide rotation relative to one another about a substantially vertical axis. First segment 314 and second segment 316 are coupled to one another for rotation about an axis which is essentially a horizontal axis and which axis is coextensive with the axes of segments 314 and 316. Joint 28 provides this rotational movement. Similarly, arm segments 316 and 318 are rotatably linked via joint 330.

A probe or pantograph-type extension 344 is mounted to the outermost segment 324 and through a belt 346 rotates in synchronism with operating instrument 338. In this fashion, probe 344 is slaved to operating instrument 338. Accordingly, a three-dimensional configuration or contour traced by the tip of operating instrument 338 will be replicated by a tip of pantograph extension 344.

Each joint 326–336 is formed to have sufficient friction to allow the joint to hold a position once placed therein. However, the friction of each joint is low enough so that movement of the joint can be commenced fairly easily.

A plurality of digital encoders 340 are mounted to arm segments 314–324. Upon a movement of operating instrument 338, encoders 340 transmit to computer 24 respective signals encoding the amount of motion in the various six degrees of freedom. The monitoring device of FIG. 14 need not include pantograph extension 344 since motion tracking is accomplished via the encoder output signals rather than optically.

Upon the transmission to computer 24 of sufficient data from surface data generating device 22 and contour data generating device 26 (FIG. 1), computer displays partial or complete graphic representations on monitor 34 of the subject tooth or teeth. The graphic representations include the visible three-dimensional surfaces of each such tooth, as well as invisible base line data fed to computer 24 by contour data generating device 26. In addition, computer 24 may be provided with electrically encoded data specifying internal structures such as the dentine inside each tooth and prior fillings or other prosthetic devices.

Upon viewing a tooth on monitor 34, a dentist may select a preparation which may be appropriate for the particular condition of the tooth. As described above, this selection may be accomplished via an instruction corresponding to an electrically encoded tooth preparation previously loaded into the memory of computer 24. Alternatively, the selection may be implemented by inputting dimensional parameters via keyboard 40, including distances, angles, planes and percentages. As another alternative, computer 24 may provide a menu selection on monitor 34, selections being made from the menu via the keyboard, a mouse or a touch-sensitive monitor screen. In yet another alternative procedure, computer 24 may be programmed to recognize structural features of the tooth, such as its type, the location and shapes of cavities and prior inlays or onlays and to automatically select a possible preparation in accordance with the recognized features. The computer may be further programmed to vary the size of the preparation to correspond to the particular tooth. The dentist would then view the selected preparation and alter it on screen by any of the above-described instruction input techniques. Upon arriving at a final, desired preparation, the dentist will inform computer via keyboard 40.

As discussed hereinabove, drill 38 (FIG. 1) is then used to remove a portion of the subject tooth. Computer 24 may control the supply of power to the drill so that the drill is operational only within the regions selected for removal during the interactive stage of the dental process. Accordingly, drill 38 will be de-energized until the cutting tip of the drill is in near engagement with a surface to be cut. Then computer 24 enables the transmission of power from supply 42 to drill 38. Upon the subsequent approach of the cutting tip of the drill to a defined boundary, as sensed preferably via data generating device 46 (FIG. 1), i.e., via CCD cameras 184, 186, 188 or 216, 218, 220 monitoring a pantograph component 50, computer 24 automatically interrupts power transmission from supply 42 to drill 38.

Figure 15:
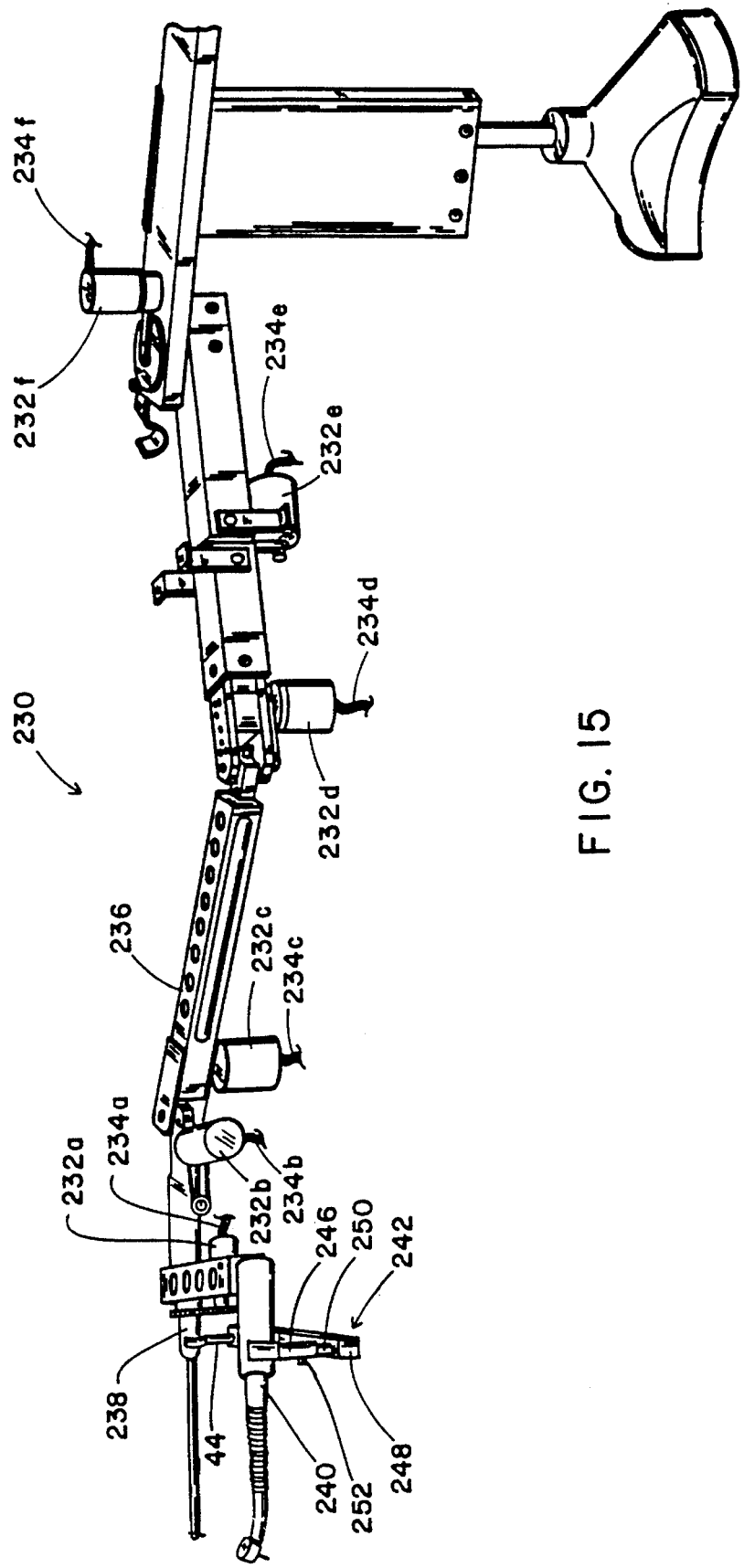
FIG. 15 is a perspective view of drill movement control assembly.

FIG. 15 illustrates a drill movement control assembly 230 similar in geometric design to the linkage 226 of FIG. 14. However, the encoders 22 of that linkage mechanism have been replaced in the movement control assembly of FIG. 15 with motors 232a–232f connected via respective energization leads 234a–234f to computer 24 (FIG. 1). In addition, in drill movement control assembly 230, the free end of a linkage 236 is connected to a pantograph arm 238 rather than to a drill member 240. Drill member 240 is rigidly but removably coupled to pantograph arm 238 via a U-shaped bridge 242 including a pair of legs 244 and 246 fastened to pantograph arm 238 and drill 240, respectively, and a transverse connector piece 248. Yet another leg member 250 is rigid with connector piece 248 and is telescopingly received inside leg 246. A spring loaded release latch 252 serves to removably clamp leg member 250 inside leg 246. Release latch 252 constitutes a safety mechanism enabling a dentist to remove drill 240 from a patient's mouth if the motion of the drill therein in response to operation of motors 232a–232f by computer 24 is not satisfactory to the dentist.

Upon the selection of a desired or optimum tooth preparation by a dentist and a subsequent signal for commencing tooth cutting, computer 24 generates a series of signals selectively energizing motors 232a–232f to move the operative end of drill 240 into engagement with those regions of the subject tooth which are to be removed to achieve the desired preparation. As described hereinabove, computer 24 controls the energization of drill 240 so that the drill is operative only in preselected zones in and about the regions of tooth to be removed.

Figure 16:
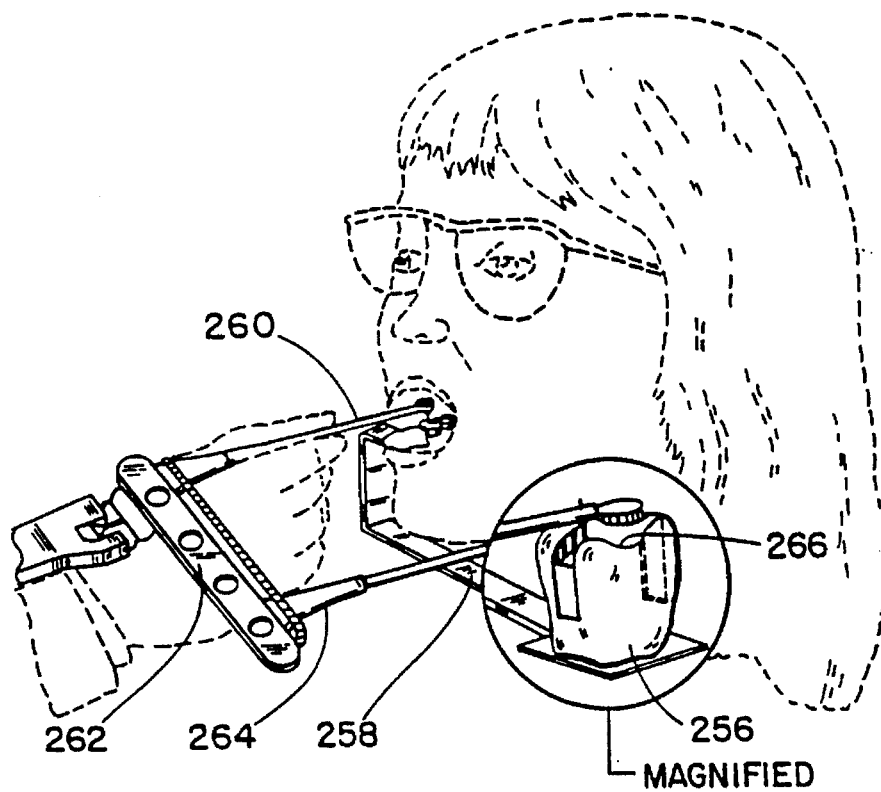
FIG. 16 is a partial perspective view, on an enlarged scale, of a drill movement restriction assembly, showing a tooth preparation preform on an even larger scale.

Limiting the motion of a dentist's drill 254 may be accomplished, as shown in FIG. 16, by selecting a tooth preparation preform 256 from a kit of preforms. Preform 256 may be selected by computer 24, as described above, to confrom to a desired preparation or may be manually selected. Preform 256 is cemented to one end of a support bracket 258, the other end of which is attached to the patient's jaw wherein is rooted a tooth to be provided with the preparation of the selected preform. A pantograph assembly including a drill 260, a bridge member 262 and a pantograph arm 264 is then used to cut the tooth. A tip on the pantograph arm corresponding to the cutting tip of drill 260 is inserted into a cavity 266 in preform 256 (in the case of a filling or inlay). Engagement of the tip of pantograph arm 264 with the walls of cavity or recess 266 limits the concomitant motion of the drill, whereby the tooth is provided with a recess having the same geometric structure as recess 266.

Accordingly, a kit is provided of dental preparation preforms in different sizes and shapes. Some preforms correspond to inlays such as that shown in FIG. 16. Other preforms corresponding to onlays or crowns. The kit may also include prefabricated restorations, that is, preformed inlays and onlays for attachment to tooth surfaces upon preparation of those surfaces as described hereinabove.

Computer 24 has a data memory loaded with electrically encoded data corresponding to all of the preformed inlays and onlays in the kit. More specifically, the predefined tooth preparations selectable automatically by computer 24 or in response to instructions received via keyboard 40 or otherwise all correspond to respective restorative inserts of several predefined sizes.

Accordingly, computer 24 operates to select a desired tooth preparation and to control the formation of that preparation in the subject tooth. Upon the completion of the preparation, either the computer or the dentist selects the appropriately sized inlay or onlay. If necessary in a particular case, a selected preformed inlay or onlay can be machined prior to attachment to a tooth. Computer 24 may control the machining operations in a conventional numerically controlled operation or may serve to limit the range of cutting motions, as described hereinabove with reference to providing a tooth with the desired preparation.

Figure 17:
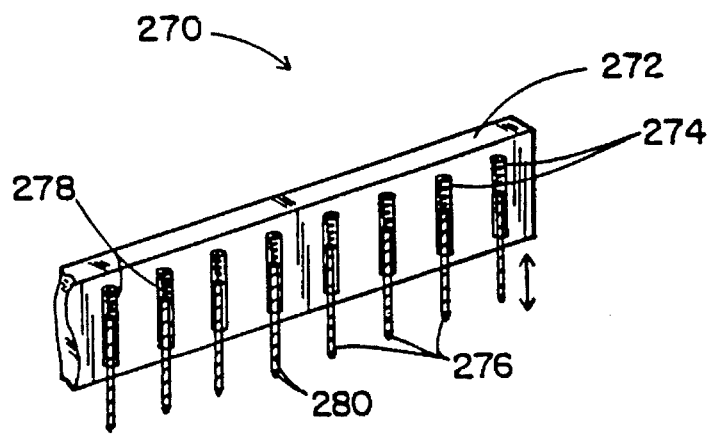
FIG. 17 is a partial schematic perspective view of a reference marker assembly.

FIG. 17 shows an assembly 270 for supplying surface data generating device 22 (FIG. 1) with optically detectable reference distances or displacements at the surface of the object (such as a tooth). Assembly 270 is attachable to the distal end of a dental probe such as instrument frame or holder 84 and comprises a holder member 272 made of transparent material and provided with a linear array of equispaced parallel bores 274 each slidably receiving a respective reference pin or stylus 276. Each stylus is pushed outwardly in a transverse direction relative to holder member 272 by a respective compression spring 278. In addition, each stylus 276 is provided with a series of longitudinally equispaced striations or reference marks 280.

The extensions of styli 276, i.e., the lengths to which the styli are pushed inside holder member 272, are measured by computer 24 through video signals obtained via a pair of optical pathways such as those illustrated in FIGS. 4 and 6. Alternatively, two optical light receiving elements such as prisms (not shown) may be placed on the same lateral side of the stylus array.

In using reference generator assembly 270 of FIG. 17, an operator such as a dentist presses styli 276 against a tooth surface. Under the pressure exerted by the operator, styli 276 are pushed respective distances into bores 274 against the action of springs 278. The displacement of each stylus 276 depends on and is a measure of a height of a respective surface element or zone of the tooth surface.

In most instances only a few (possibly as few as two) different positionings of stylus assembly 270 are required for computer 24 to map the entire surface of the tooth under observation.

FIG. 18 illustrates one method of applying reference markings to the surface of a tooth or tooth preparation for purposes of providing a distance standard for data generating device 22 (FIG. 1). The reference markings in this case take the form of a grid 402 of a first set of parallel lines 404 and a second set of parallel lines 406, the first set being substantially orthogonal to the second set. Grid 402 is printed or otherwise disposed on a strip or tape 408 which is attached to a surface 410 (e.g., a buccal surface) of a tooth 412 (e.g., a molar) via a layer of adhesive (not shown).

FIG. 19 shows, on surface 410 of tooth 412, another reference marker applicator in the form of a tape strip 414 provided with a plurality of transversely extending slits 416 and, between the slits, with identification markings 418 in the form of bar codes. Slits 416 are of identical size and orientation and are spaced from one another by a known distance. In addition, because tape strip 414 has a uniform thickness, the depth of slits 414 is known. The known depth of slits 414 provides a particularly precise reference distance at the surface 410 of tooth 412. Furthermore, identification markings 418 serve to automatically provide computer 24, via data generating device 22, with information pertaining to the type of tooth (molar) and the surface (buccal), as well as the location of tooth 412 in the patient's mouth and perhaps also the relative location with respect to a tooth or teeth to be restored.

FIG. 20 depicts, again on surface 410 of tooth 412, yet another reference marker applicator similar to that illustrated in FIG. 19. In FIG. 20, the reference marker applicator is a tape strip 420 provided with a plurality of relatively staggered, longitudinally extending slits 422 and, between the slits, with identification markings 424 in the form of bar codes. Slits 422 are preferably of identical size and orientation and are spaced from one another, both in the transverse direction and the longitudinal direction, by known distances. In addition, because tape strip 420 has a uniform thickness, the depth of slits 422 is known. The known depth of slits 422 again provides a precise reference distance at the surface 410 of tooth 412. As described hereinabove, the identification markings 424 serve to automatically provide computer 24, via data generating device 22, with information as to the tooth type, surface, location in the patient's mouth and with respect to a projected restoration.

A tape strip 426 with slits 428 and reference markings 430 is shown in exagerrated detail in FIG. 21. Also illustrated in that drawing figure is an adhesive layer 432 for temporarily fixing the tape strip 426 to a mouth or dental surface. It is to be noted that tape strip 426, as well as any other similar tape strip or reference mark applicator described herein, may be applied to gum and palate surfaces instead of to original tooth or restoration surfaces. In such a case, the identification markings carried on the tape are appropriate to the surface to which the reference marking application is being attached.

As illustrated in FIG. 22, yet another reference marking applicator comprises a tape strip 434 provided with a plurality of longitudinally extending slits 436 and, between the slits, with identification markings 438 in the form of bar codes. Slits 436 are preferably of identical size and orientation and are spaced from one another, both in the transverse direction and the longitduinal direction, by known distances. Tape strip 434 has a uniform thickness; consequently, the depth of slits 436 is known and can be programmed or entered into computer 24. The known depth of slits 436 thus provides computer 24 with an exact reference distance. As described hereinabove, the identification markings 424 serve to automatically provide computer 24, via data generating device 22, with information as to the tooth type, surface, location in the patient's mouth and with respect to a projected restoration.

As shown in FIGS. 23 and 24, a device for facilitating the attachment of a reference tape such as tape 408, 414, 420, or 426 to a surface (e.g., buccal surface 410) of a tooth (e.g., molar 412) comprises an elongate body 440 formed at a distal end with a chamber 442. Chamber 442 houses at a proximal end a roll 444 of reference marking applicator tape 446, the roll being rotatably secured to body 440 by a shaft 448. Body 440 may be provided with a door (not illustrated) for facilitating the replacement of tape roll 444 with another roll of the same kind of tape (e.g., the same identification markings) or a roll of a different kind of tape. Alternatively, the device may include means for attaching a cartridge, wherein different cartridges hold tapes for different applications, such as for different mouth surfaces.

As further shown in FIGS. 23 and 34, a distal end of chamber 442 contains a tape gripping and transport mechanism 450. Mechanism 450 includes a pair of wheels 452 and 454 (FIG. 24) which project slightly through an opening 456 in body 440 at the distal end of chamber 442. Wheels 452 and 454 are rotatably mounted to side walls 458 and 460 of body 440 via a shaft 462 and are rigid with respect to a cylinder 464 in which a plurality of pins 466 are embedded. During a movement of the distal end of the instrument or device across a mouth surface, pins 466 grippingly engage tape 446. Rotation of wheels 452 and 454, caused by friction contact with a relatively moving mouth surface, causes cylinder 464 to rotate and pins 466 to pull tape 446 from roll 444 towards the distal end of the instrument. Tape 446 is wedged between spiked cylinder or roller 464 and a contoured internal piece 468.

Distally of tape transport mechanism 450, tape 446 is pressed against a dental surface through the action of a lever arm 470 rotatably secured to body 440 via a pivot pin 472. Lever arm is rotated in the direction indicated by an arcuate arrow 474, in response to a distally directed movement of an actuator strip 476. Actuator strip 476 is pivotably secured at a distal end to lever arm 470 at 478 and is attached at a proximal end to an actuator knob 480. Manual pressure on actuator knob 480 in the direction of arrow 482 causes a swinging of lever arm 470 so that a sharpened tip or edge 484 at the free end 486 of the lever arm contacts one side of a plate 488. A free end of tape 446 is located on the other side of plate 488, whereby application pressure is applied to tape 446 via lever arm 470 and plate 488. Plate 488 is integral with a distal end of a preformed spring metal strip 490 in turn connected at a proximal end to a second actuator knob 492.

Upon the application of a length of tape 446 to a tooth surface, actuator knob 492 is manually pulled in the direction of arrow 494, thereby removing plate 488 from between the tape and the sharpened tip or edge 484 of lever arm 470. Actuator knob 480 is then pushed in the distal direction, as indicated by arrow 482, to pinch tape 446 at the distal end thereof against the tooth surface. This pinching action results in a severing of the free end of tape 446 by sharp edge 484. Upon the completion of the tape cutting operation, actuator knob 492 is pushed back in the distal direction, whereupon the applicator instrument is ready for another tape application operation.

FIG. 25 shows a simpler device for use in applying a strip of reference marker bearing tape (e.g., tape 426 in FIG. 21) to a tooth or gum surface. The applicator device comprises a body portion 496 provided on an outer side with a handle grip 498 and formed on an inner side with an arcuate applicator surface 500 essentially conforming to the tooth, gum or other mouth surface to which the reference marker tape strip is to be applied. A dental practitioner may be provided with a kit of such applicator forms, a plurality of forms being included for each mouth surface. For example, an occlusal or lingual surface of an upper molar or a lower incisor will have on the order of a dozen forms in different sizes and shapes, as will other mouth surfaces.

In using the appicator device or form of FIG. 25, a dentist or technician disposes a tape strip on the curved applicator surface 500 or, alternatively, on the tooth surface to which the tape is to be applied. The tape strip is then pressed against the tooth surface via the applicator form.

It is to be noted that reference marker bearing tape strips may be tinted or otherwise coated with an off-white, gray or a hued coloring in order to reduce glare. The reduction of glare facilitates the input of contour information via data generating device 22.

Successive steps in yet another method for applying reference marker tape strips to teeth and other features in the mouth is illustrated in FIG. 26. A clump of wax 502 or other impression forming material is placed over the mouth surface or surfaces, as indicated by an arrow 503. In the example of FIG. 26, the relevant mouth surfaces include occlusal surfaces of two intact molars 504 and 506 and an intact bicuspid 508, as well as a prepared molar 510. The clump of wax is manipulated so that an impression 512 is taken of the subject tooth surfaces. The wax is then removed, as indicated by an arrow 514. A hardenable liquid dental material 516 from a reservoir 518 is then deposited onto the impression surface 512 of the piece of wax 502. In a subsequent step, the piece of wax 502 is replaced on the teeth so that the hardenable liquid material takes the form of a thin layer 520 conforming to the impression 512 and therefore to the subject tooth surfaces. Upon the hardening of the coating layer 520, the piece of wax 502, with the hardened coating layer 520, is removed (not shown). In a subsequent step, one or more reference marker tape strips 522 are placed between the subject teeth 504, 506, 508 and 510, on the one hand, and the hardened coating layer 520 in the piece of wax 502, on the other hand. As indicated by an arrow 524, the piece of wax 502 is pressed against the tape strips 522 which in turn are pressed against the subject tooth surfaces. Because coating layer 520 has the exact shape of the subject tooth surfaces, tape strips 522 are pressed throughout their entire extent against those tooth surfaces, thereby optimizing adherence of the tape strips to the teeth.

As depicted in FIG. 27, an applicator member for facilitating the provision of distance reference marks and/or identification markings at a mouth surface comprises a central section 526 having a plurality of appended tape strips 528a, 528b, 528c and 528d connected thereto. As shown in FIG. 28, central section or hub 526 is designed for attachment to a particular tooth surface, such as the occlusal surface 530 of a molar 532, while tape strips 528a, 528b, 528c and 528d are adapted for attachment to different side surfaces, such as an interproximal, a buccal, another interproximal and a lingual surface, respectively. Each tape strip 528a, 528b, 528c and 528d is accordingly provided with slots and identification markings (not illustrated) identifying the respective tooth surface (interproximal, buccal, interproximal and lingual) and the particular tooth (e.g., upper right first molar). Central section or hub 526 is also provided with identifying markings and slots or slits (not shown). A kit of such adhesively attachable cross-, star- or wheel-shaped reference marker elements may be provided for dental practitioners.

FIG. 29 illustrates a variation of the reference marker element of FIGS. 27 and 28. In FIG. 29, a thin metallic body member 534 is connected to a plurality of elongate extensions or arms 536a, 536b, 536c, 536d each provided on one side with an adhesive layer and further provided with slits or slots and identification markings (not illustrated), as described above. The reference marker element of FIG. 29 is used by sliding the metallic body member 534 between two adjacent teeth and folding the extensions or arms 536a, 536b, 536c, 536d over occlusal and lingual or buccal surfaces of teeth. Extensions or arms 536a, 536b, 536c, 536d may be pressed to the respective tooth surface by an application member such as that illlustrated in FIG. 25. Alternatively, a conventional dental instrument with a blunt edge may be utilized.

As shown in FIG. 30, a device for applying reference markers to the surface of a tooth (e.g., a molar) comprises a crown-shaped member 538 formed with a plurality of score lines 540 and one or more tabs 542, 544. As further shown in the cross-sectional view of FIG. 31, crown-shaped member 538 includes an inner adhesive layer 546, a second layer 548 of transparent or translucent polymeric material in which reference distance markings and identification markings (not shown) are embedded, another adhesive layer 550 and an outer layer of polymeric material 552.

Upon the disposition of crown-shaped reference marker applicator member 538 over a similarly shaped tooth and the application of pressure, for example, by means of a blunt dental instrument, to ensure a bond-forming contact between inner adhesive layer 546 and the various surfaces of the tooth, tabs 542 and 544 are pulled, thereby tearing polymeric layer 552 along score lines 540. Inasmuch as adhesive layer 546 is stronger than adhesive layer 550, the tearing of polymeric layer 552 removes that layer from the tooth, while leaving marker bearing strips of layer 548 intact on the tooth surfaces.

It is to be noted that dental practitioners may be provided with kits of such multiple preformed tooth-shaped applicator members for temporarily attaching reference and identification marker elements to tooth surfaces. Each kit includes a plurality of preformed applicators for each tooth, which take into account basic variations in the shape of that tooth as well as different sizes thereof. In using such a kit, the dental practitioner or aide selects the preformed applicator member which is closest in shape and size to the subject tooth. In the event the selected applicator member deviates from an outer surface of the tooth, the applicator member may be deformed by the practitioner to assume the tooth's shape and thereby press the inner adhesive layer 546 against the tooth.

It is to be further noted that marker bearing layer 548 (as well as adhesive layers 546 and 550) may be formed as an array of separate segments each corresponding to a respective tooth surface. The separate segments are held in a predetermined pattern or array by outer polymeric layer 552.

As shown in FIG. 32, an applicator member 554 may be provided for attaching reference marker strips or segments to surfaces of a prepared tooth. The structure and use of applicator member 554 is similar to that of the applicator member of FIG. 30. Applicator member 554 has a four-part layer structure (see FIG. 31) and at least one pull tab 556 for facilitating the removal of the outer polymeric layer (552, FIG. 31) upon the application of application member 554 to a prepared tooth.

Figure 33:
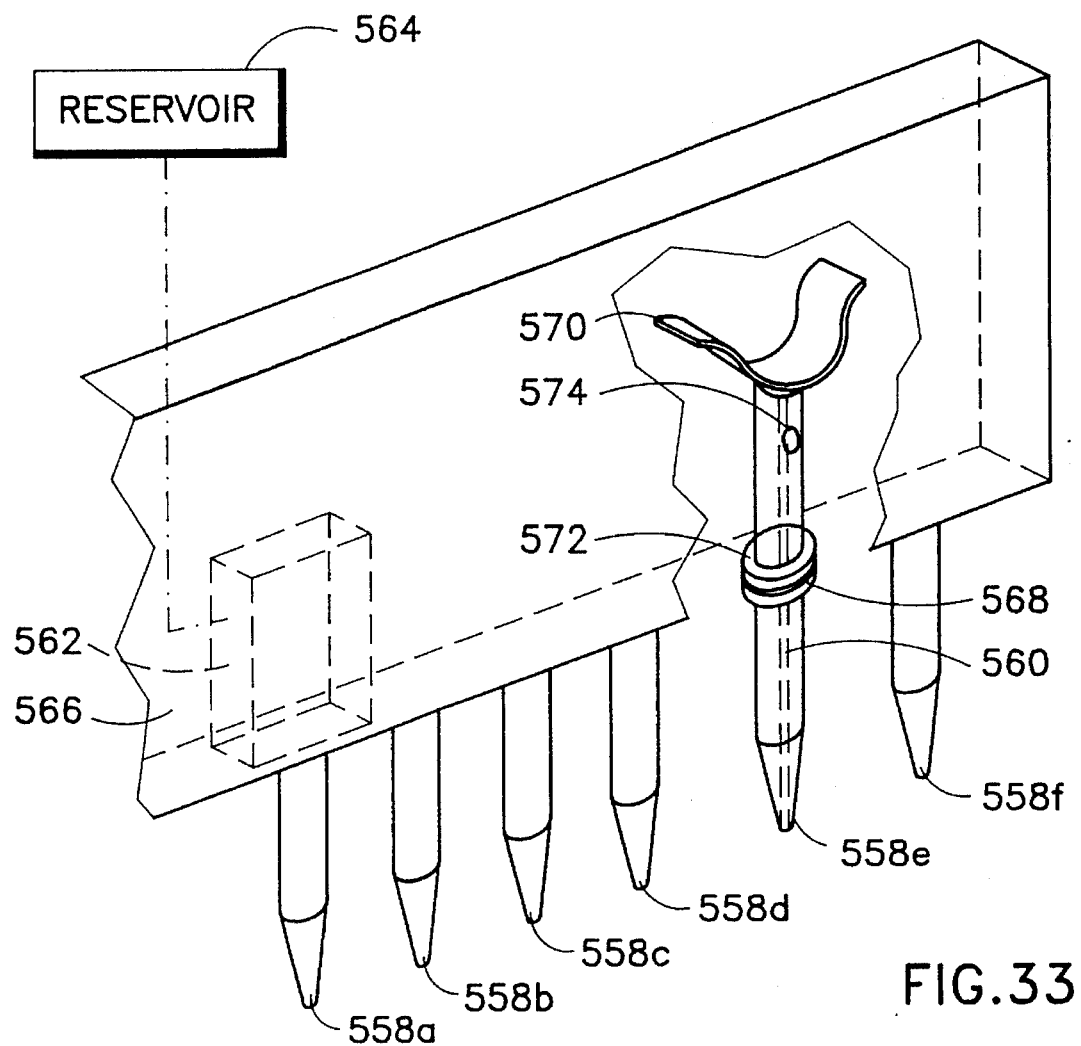
FIG. 33 is a partial perspective view, on an enlarged scale and partially broken away, of another device for applying reference markings to a mouth surface.

FIG. 33 depicts another device for applying reference markings to a mouth surface. Basically, the device comprises a plurality of elongate pointed applicator members 558a, 558b, 558c, 558d, 558e, 558f each formed with a respective axial channel 560. At an inner end, each pointed member 558a, 558b, 558c, 558d, 558e, 558f is disposed inside a chamber 562 which containing a nontoxic marking fluid replenishable, for instance, from a reservoir or supply 564. Reservoir 564 may be located inside a handle or holder component 566 of the marking device.

Applicator members 558a, 558b, 558c, 558d, 558e, 558f extend parallel to each other and are disposed on holder or frame 566 in a linear array. Accordingly, upon pressing of the tips of the applicator members 558a, 558b, 558c, 558d, 558e, 558f against a mouth surface and upon a movement of the holder or frame 566 generally in a direction perpendicular to the linear array of applicator members 558a, 558b, 558c, 558d, 558e, 558f, a plurality of parallel lines are placed on the moth surface, following the contours thereof.

Applicator members 558a, 558b, 558c, 558d, 558e, 558f are provided with a respective ring seal 568 at the base of the respective fluid containing chamber 562. In addition, each applicator member 558a, 558b, 558c, 558d, 558e, 558f is biased into an outward or extended position by a respective leaf spring 570. The outward motion of each applicator member 558a, 558b, 558c, 558d, 558e, 558f is arrested by a respective collar 572 which engages the respective ring seal 568. Leaf springs 570 ensure that applicator members 558a, 558b, 558c, 558d, 558e, 558f follow the contour of the surface being marked.

Channels 560 each communicate at an inner end with the respective fluid-containing chamber 562 via one or more ports 574, whereby marking fluid flows from chamber 562 to the tips of applicator members 558a, 558b, 558c, 558d, 558e, 558f.

It is to be noted that applicator members 558a, 558b, 558c, 558d, 558e, 558f are essentially spring loaded pens and may be formed as such. For example, each applicator member may be provided with a felt tip or other component for ensuring an application of ingestible and removable ink to a mouth surface.

As illustrated in FIGS. 34 and 35, a tape strip 576 for facilitating tracing of a tooth contour with pantograph-type data generating device or assembly 26 (FIG. 1) is provided on one side with an adhesive layer 578 and on an opposite side with a plurality of parallel ridges or beads 580 defining a series of parallel shoulder for guiding the tip of stylus member 52 (FIG. 1) along the surface of a tooth or other mouth surface.

As illustrated in FIG. 35, tape strip 576 may be further provided with identification markings 582, as described hereinabove with reference to FIGS. 19–22, for identifying the different mouth surfaces to which the tape strip is applied. Clearly, different rolls of tape strip 576 are provided for different types of tooth surfaces. Thus, a practitioner may be furnished with a kit having several rolls of contour guide tapes for each tooth.

It is to be noted that the slits or slots 416, 422 428 and 436 in reference marker tape strips 414, 420, 426 and 434 (FIGS. 19–22) may function as guides for stylus member 52 of data generating device or assembly 26. The side walls of the slits or slots thus serve as shoulders for guiding the movement of stylus member 52 along a plurality of parallel lines.

It is to be further noted that ridges as in tape strip 576 and slots as in tape strip 22 may be combined in a single tape strip to facilitate both the collection of three-dimensional video data with data generating device or assembly 22 and the collection of three-dimensional contour data with data generating device or assembly 26. Both slots and ridges may extend in the longitudinal direction, with ridges alternating with slots in the transverse direction.

FIGS. 36 through 42 all illustrate devices intended for use by a dental practitioner or laboratory personnel to aid in the manual modification of teeth or restorations. Generally, each embodiment of a tooth preparation or dental restoration modification apparatus described hereinafter includes a light projection device or assembly operated under computer control for illuminating a point on the surface of a tooth or restoration which is to be drilled or otherwise machined to remove excess material. The computer determines the locations of excess material on the tooth or restoration and operates the light projection assembly to successively illuminate different locations of excess material. Via opto-electrical transducers or charge-coupled devices 72 and 74 (FIG. 1), computer 24 monitors pantograph component 64 and concomitantly monitors the motions of the tip of drill 38 inside the mouth and even inside a tooth. Upon determining that a desired amount of dental material has been removed, computer 24 shifts the illuminating beam from one location to the next.

As discussed hereinabove, computer 24 (FIG. 1) obtains digitized data as to surfaces and contours of a tooth via optical data generating device 22 and pantograph data generating device 26. In addition, computer 24 is preferably preprogrammed with data specifying three dimensional surface shapes of tooth restoration preforms in a kit of such preforms. From this data, computer 24 is able to determine the points of excess material on a tooth and a restoration preform selected either by the computer or by the dental practitioner to be attached to the tooth during the restorative dental operation.

Figure 36:
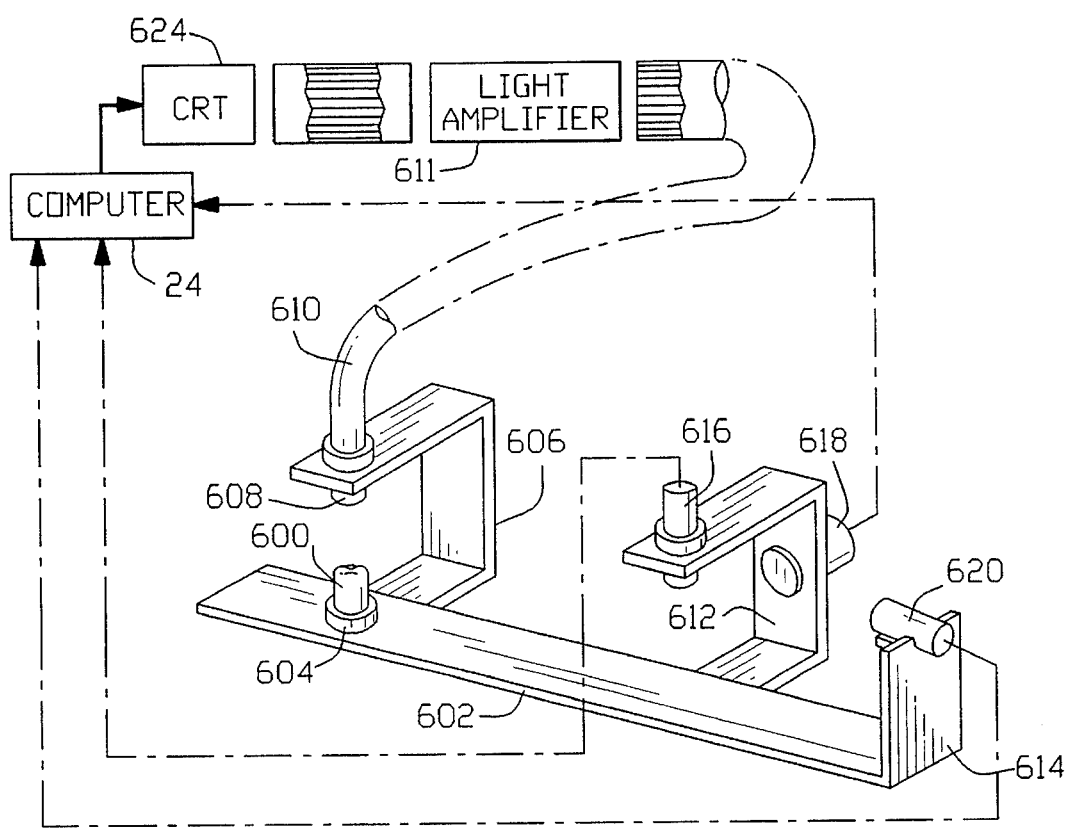
FIG. 36 is partially a block diagram and partially a schematic perspective view of an apparatus for modifying a dental restoration in accordance with the present invention.

As illustrated in FIG. 36, an apparatus for assisting a dentist or lab technician in modifying a dental restoration preform 600 comprises a frame 602 provided with a collar or other holder 604 for maintaining the preform 600 in a predetermined fixed position. An arm 606 of frame 602 supports a free end 608 of a fiber optic cable 610 so that light from the optical fibers of cable 610 projects upon an exposed surface (e.g., an occlusal surface) of the dental restoration preform 600.

Frame 602 also carries a pair of additional arms 612 and 614 together supporting a plurality of cameras in the form of charge-coupled devices ("CCD's") 616, 618 and 620. CCD cameras 616, 618 and 620 are operatively connected to a computer, which is preferably computer 24 (FIG. 1) if the tooth preparation or dental restoration modification apparatus is installed for use at a dentist's office.

Computer 24 is connected to a light source 624 exemplarily in the form of a cathode ray tube or an LED array which in turn is operatively coupled (e.g. juxtaposed) to a proximal or input end of cable 610. By properly comtrolling light source 624, computer 24 induces the transmission of light along one or more selected fibers of cable 610.

Prior to attaching a preformed dental restoration to a prepared tooth, the dental practitioner (or lab technician) mounts the preformed restoration to frame 602 via collar or holder 604. Upon completion of calibration and initialization steps such as informing computer 24 of the identity of preform 600 and the orientation of the preform with respect to frame 602, computer 24 is then operated to determine the points of excess material on the restoration preform. As described hereinabove, that determination entails computation of the differences between the surfaces of preform 600 and corresponding surfaces of the tooth to which the preform is to be attached. In addition, the dental restoration may be modified to conform to the contours of opposing teeth (adjusting the bite).

Computer 24 transmits a signal to light source 624 causing the illumination, via cable 610 and possibly a light amplifier 611, of a point on the surface of preform 600 which represents excess material. The dentist then uses pantograph assembly 64 to guide drill 38 to the illuminated location to remove the excess material. The progress of the material removal operation is monitored by computer 24 via pantograph extension 66 (FIG. 1) and CCD cameras 616, 618 and 620. Upon the removal of the excess material, computer 24 terminates the transmission of light along the previously selected fiber of cable 610. If, however, the dental preform 600 has further excess material, computer 24 successively illuminates selected other optical fibers of cable 610 until all of the excess material has been removed.

Moreover, computer 24 may be programmed to illuminate fibers of cable 610 only upon the approach of drill 3 and pantograph assembly 64 to within a predetermined distance from collar 604 and preform 610.

Figure 37:
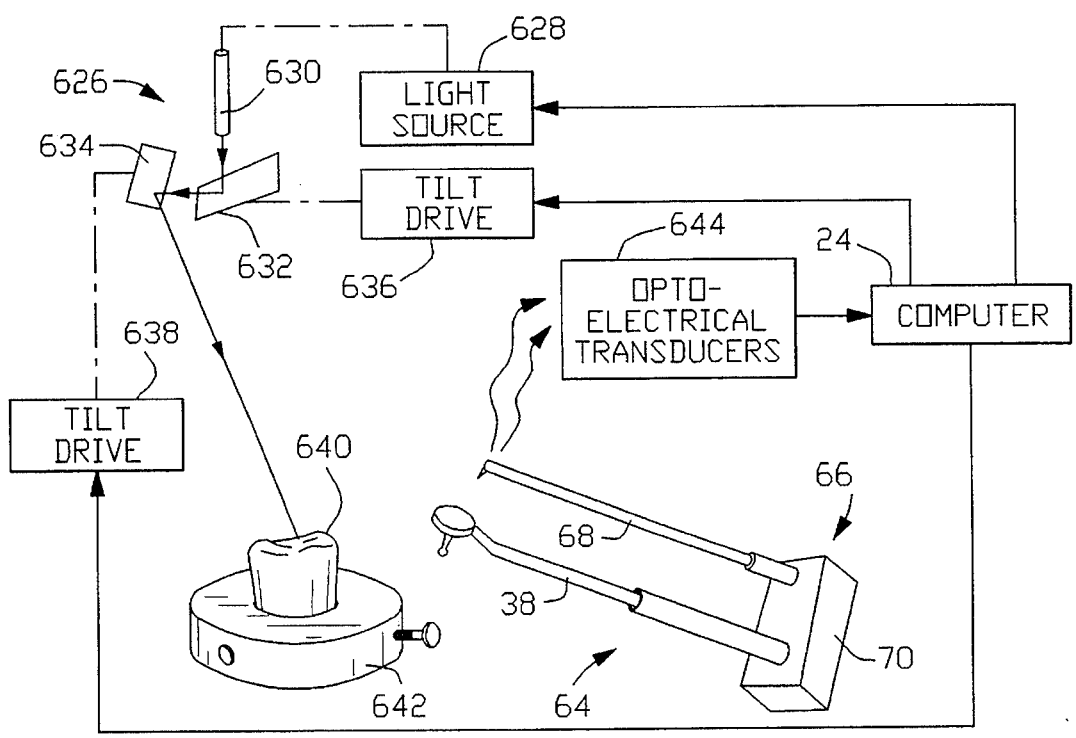
FIG. 37 is partially a block diagram and partially a schematic perspective view of another dental restoration modification apparatus in accordance with the present invention.

As depicted in FIG. 37, another apparatus for assisting a dentist or technician in the modification of a dental restoration preform comprises a light projection assembly 626 including a light source 628 (e.g., a laser device), an optical fiber 630, a pair of optical elements in the form of pivoting mirrors 632 and 634, and two rotary drives 636 and 638 operatively connected to mirrors 632 and 634 for tilting them in response to control signals received from computer 24. By appropriate orientation of mirrors 632 and 634, computer 24 is able to direct a beam of light onto a computed location on a dental preform 640. Preform 640 is mounted to a collar or holder element 642 which is stationary with respect to a plurality of opto-electrical transducers (CCDs) 644. Transducers 644 transmit to computer 24 electrical signals identifying the location of pantograph assembly 64 and drill 38 (FIG. 1) with respect to holder 642 and preform 640. In response to those position identification signals, computer 24 initiates or terminates the projection of a light beam onto preform 640, as discussed above with respect to FIG. 36.

Figure 38:
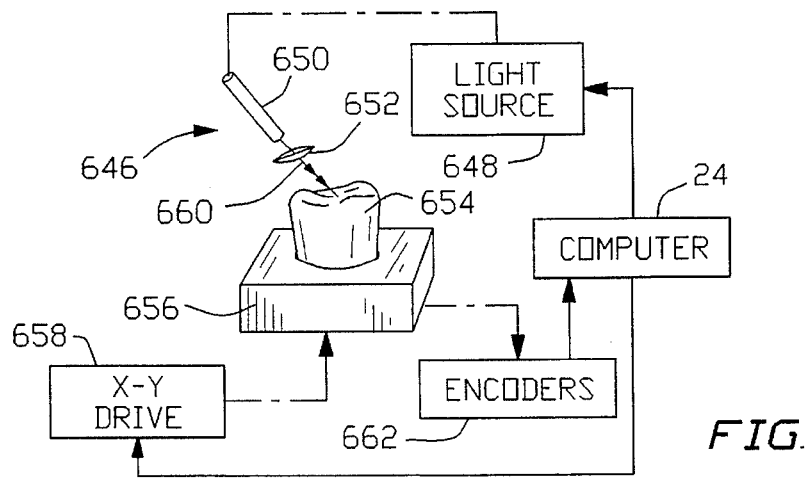
FIG. 38 is a diagram of yet another dental restoration modification apparatus in accordance with the present invention.

As illustrated in FIG. 38, yet another apparatus for assisting a dentist or technician in the modification of a dental restoration preform comprises a light projection assembly 646 including a light source 648, an optical fiber 650, and a focusing lens 652. A dental preform 654 is mounted to a table 656 which is shiftably mounted to a stationary stage or platform (not illustrated). Computer 24 is operatively connected to an X-Y drive 658 for shifting table 656 to position preform 654 so that a precalculated spot thereon is placed in the path of a beam of light 660 emitted by light projection assembly 646. Computer 24 obtains feedback as to the location of table 656 via encoders 662. As discussed above with reference to FIG. 37, opto-electrical transducers 644 provide computer 24 with digitized data as to the location of pantograph assembly 64 and drill 38.

Figure 39:
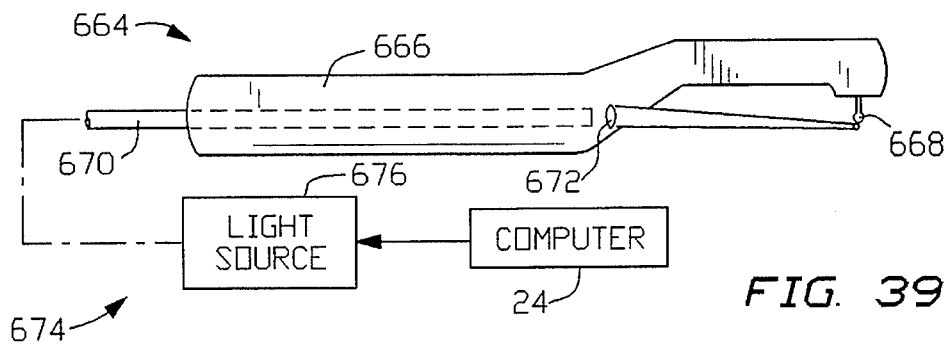
FIG. 39 is partially a block diagram and partially a side elevational view of an apparatus for assisting in the preparation of a tooth in accordance with the present invention.

FIG. 39 schematically depicts a dental drilling instrument 664 for use in assisting a dentist in preparing a tooth. Instrument 664 is preferably designed to be used in conjunction with pantograph assembly 64 (FIG. 1) and includes a handle or grip 666 for guiding a drill bit 668 to a desired location to remove enamel or other material from the surface of a tooth. Instrument 664 is further provided in handle 666 with the distal end of an optical fiber 670 and a lens 672 for focusing a beam of light from light fiber 670 onto a point at the free end of drill bit 668.

Optical fiber 670 forms a portion of a light projection assembly 674 further including a light source (e.g., laser device) 676. Computer 24 is operatively connected to light source 676 for alternately energizing and de-energizing that source in accordance with the location of drill bit 668 and particularly the operative end thereof, as determined by computer 24 from a stereophotogrammetric triangulation program operating on digital signals from opto-electrical transducers (CCDs) 644 (FIG. 37). Computer 24 thus causes the emission of a spot of light at the tip of drill bit 668 upon the approach of that tip towards a point of excess material on a subject tooth. The spot of light illuminates the point of excess material and thereby directs the dentist to successive tooth locations which require material removal. Upon the completion of the removal operation, computer 24 de-energizes light source 676 and thereby terminates the projection of light to the tip of drill bit 668.

Figure 40:
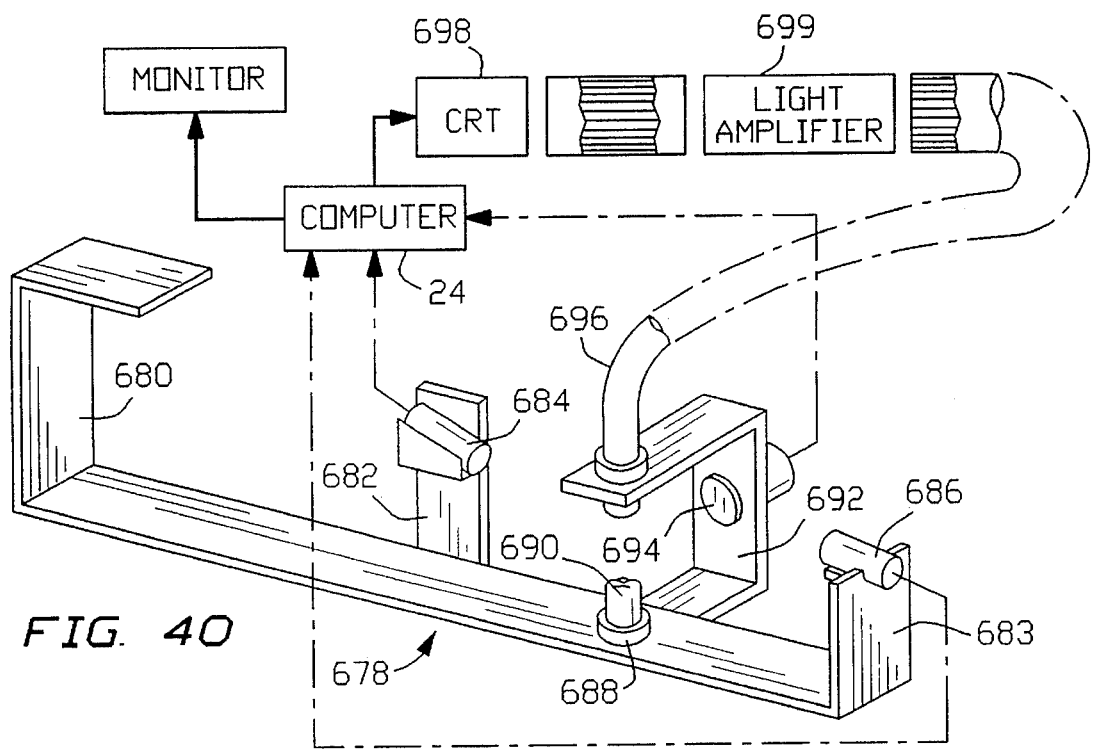
FIG. 40 is partially a block diagram and partially a schematic perspective view of another tooth preparation apparatus in accordance with the present invention.

As shown in FIG. 40, another dental preparation apparatus comprises a frame structure 678 with an arm 680 for enabling attachment of the frame to a person's jaw. Another two arms 682 and 683 spaced from jaw attachment arm 680 are provided on frame 678 for carrying respective charge coupled devices 684 and 686 directed at different angles towards a dental preform mounting bracket 688. Bracket 688 holds a dental preform 690 in the form of a tooth under preparation by a dentist. Another support arm 692 is rigid with frame 678 and carries a third charge coupled device 694, as well as an output end of a cable 696 of optical fibers. As discussed hereinabove with reference to FIG. 36, optical cable 696 extends from a light source 698 such as a CRT display or a two-dimensional LED array. Light source 698 (and/or a light amplification unit 699) is operated by computer 24 so as to illuminate a predetermined point on the surface of preform 690, thereby informing the dentist as to a location of excess material on the corresponding tooth. The tip of pantograph arm 68 (FIG. 1) of pantograph assembly 64 is preferably formed to avoid contact with preform 690 during preparation of the tooth corresponding to that preform. Alternatively, pantograph arm 68 may take the form of a drill instrument for cutting into preform 690 simultaneously with the preparation of the subject tooth. To that end, preform 690 may be formed of a material which is soft and easy to cut.

Pursuant to the embodiment illustrated in FIG. 40, support arms 682, 683 and 692 and mounting bracket 688 are positioned so that preform 690 is machinable while the subject tooth is being drilled. Alternatively and perhaps preferably, bracket 688 and the free or distal end of optical fiber cable 696 may be located at another position along frame structure 678 spaced from both the patient's jaw and support arms 682, 683 and 692.

Computer 24 uses optical fiber cable 696 and preform 690 to communicate to a dentist instructions as to locations for removing excess amterial from a tooth. In accordance with another alternative, computer 24 communicates the locations of excess material on a subject tooth by displaying an image of the tooth, together with highlighted excess points, on monitor 34 (see FIGS. 1 and 40). Instruction in this regard may be implemented according to any desired protocol. For example, all the points of excess material may be displayed initially. Subsequently, different points may be highlighted successively as the modification work proceeds.

Figure 41:
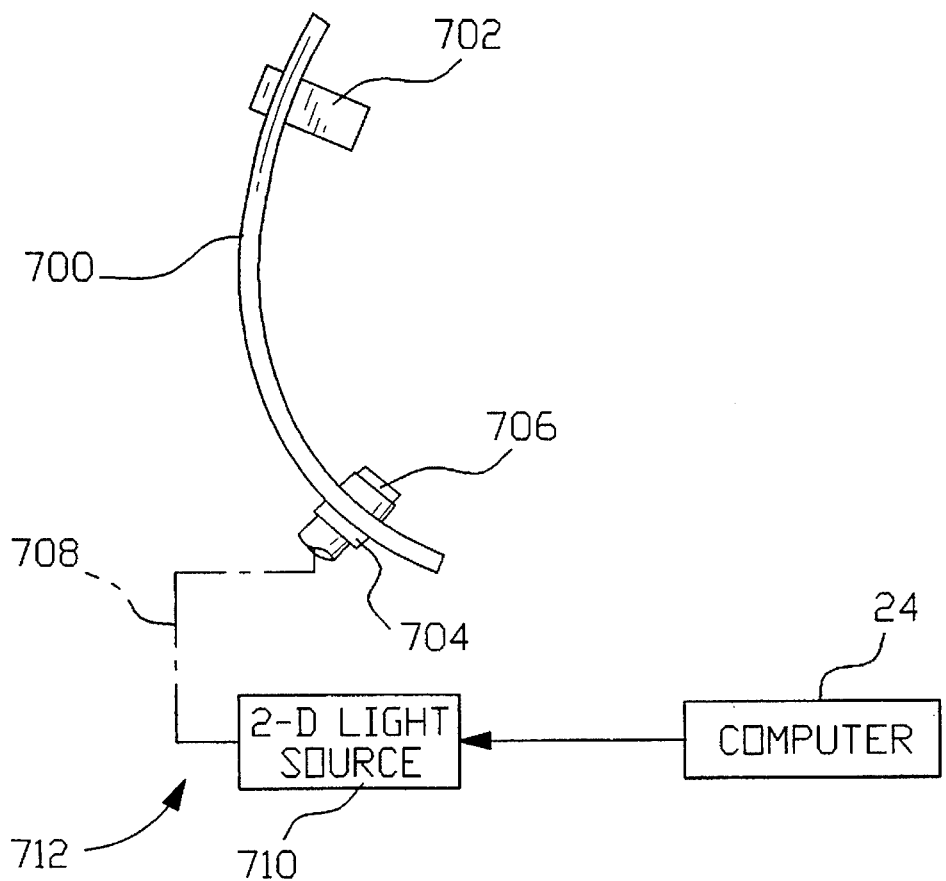
FIG. 41 is partially a top view and partially a block diagram of a further tooth preparation apparatus in accordance with the present invention.
Figure 42:
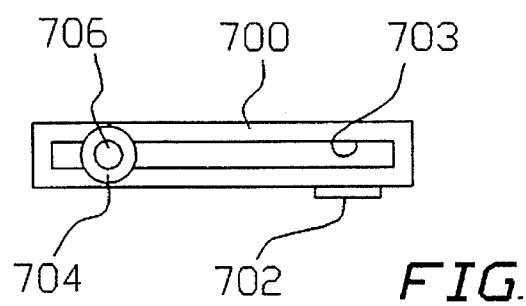
FIG. 42 is a side elevational view of a portion of the tooth preparation apparatus shown in FIG. 41.

The instructional aid embodied in the computer 24 and monitor 34, or in the optical fiber cable 696 and bracket 688 with preform 690, may be used in conjunction with the tooth preparation apparatus illustrated in FIG. 39 or an alternative apparatus shown schematically in FIGS. 41 and 42. In the latter case, an arcuate track or rail 700 is mountable to a patient's jaw, e.g., via an arm 702, so that the rail extends parallel to the patient's dentition. Rail 700 is formed with a longitudinal slot 703 which receives a fitting 704 at the output or distal end 706 of an optical cable 708. Individual fibers of cable 708 are illuminated to carry light beams by a two-dimensional light source 710 under the control of computer 24.

Upon an attachment of bracket or arm 702 to the patient's jaw and an adjustment of fitting 704 so that output end 706 of optical cable 708 is opposite a desired tooth, pantograph assembly 64 is used to calibrate an optical projection assembly 712 including cable 708 and source 710. The calibration entails informing computer 24 of the location and orientation of distal cable end 706 relative to the subject tooth. If necessary, the computer can instruct the dentist to relocate the cable fitting 704 to improve alignment with the subject tooth. Upon completion of the calibration process, computer 24 controls a selective illumination of points on the surface of the tooth, thereby instructing the dental practitioner to remove excess tooth material at the locations determined by computer 24 in accordance with (a) digitized surface data as to the tooth and possibly as to a preform which has been modified via drill 38 and pantograph assembly 64 (see FIGS. 36, 37 and 38 and accompanying description), (b) preprogrammed preform data, and (c) instructions communicated by the dentist to computer 24 via keyboard 40 (FIG. 1) or other input device. Rail 700 is particularly adapted for the illumination of labial or buccal surfaces. However, by a slight modification, i.e., by providing rail 700 with a channel shaped cross-section, occlusal and lingual surfaces may be covered as well. It is to be understood that the distance of rail 700 and output end 706 of cable 708 from the subject tooth surface is great enough to permit insertion of drill 38 of pantograph assembly 64 between the tooth and the end of the optical cable.

As illustrated in FIG. 1, a voice-recognition unit 714 is advantageously connected to computer 24 for facilitating data input into the computer. Voice recognition unit 714 may be implemented as an off-the-shelf device and will generally include an acousto-electrical transducer or microphone 716 working into an analog-to-digital converter 718. Transducer 716 and converter 718 cofunction to provide computer 24 with electrical signals encoding incoming voice-frequency sounds. Computer 24 is provided with a conventional voice-recognition program, modified to identify, encode and respond to specific voice commands useful in the dentist's office. Such commands, for example, identify the teeth the dentist is working on, so that the dentist need not pause in the use of data generating devices 22, 26 and 36 in order to enter information into computer 24 via kjeyboard 40. Instead, as the dentist begins to trace a tooth with pantograph assembly 50 or to scan the tooth with device 22, he or she pronounces the words "scanning tooth" together with a number identifying the particular tooth the dentist is examining. Other commands may also be fed to computer 24 via voice-recognition unit 714.

Figure 43:
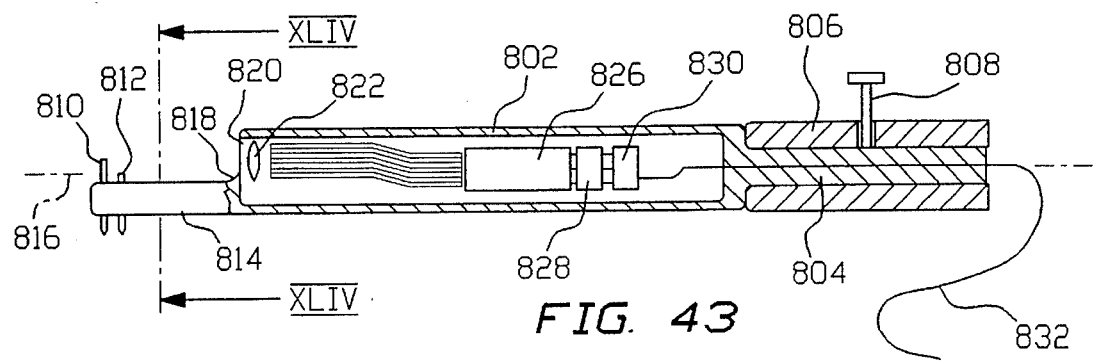
FIG. 43 is a side elevational view, partially in cross-section, of a hand held instrument usable in conjunction with a pantograph assembly illustrated in FIGS. 11–15, for gathering parallel contour data, in accordance with the present invention.

As illustrated in FIG. 43, a device for feeding to computer 24 (FIG. 1) contour data as to the surface of an object such as a tooth comprises a hand-held dental instrument or frame 802 provided at a proximal end with an extension 804 removably insertable into a sleeve 806 which forms a part of a pantograph assembly such as that illustrated in FIGS. 11 through 15. Instrument frame 802 is locked in a predetermined position and orientation to pantograph sleeve 806 by a set screw 808.

At a distal end, instrument frame 802 carries two sets of pins 810 and 812 slidably mounted to a nose portion 814 of instrument frame 802 in respective linear arrays extending at an angle, preferably a right angle, with respect to a longitudinal axis 816 of instrument frame 802.

Proximally of nose portion 814, instrument frame 802 has a shoulder 818 in turn formed with an opening or window 820 facing pins 810 and 812. A lens 822 is disposed at window 820 for focusing incoming light on an input end of a bundle of optical fibers 824 extending to a charge coupled device ("CCD") 826 inside instrument frame 802. CCD 826 is provided with conventional scanning circuitry 828 and output signal preprocessing circuitry 830. An output lead or multiple 832 extends from preprocessing circuitry 830 to computer 24 (FIG. 1).

Figure 44:
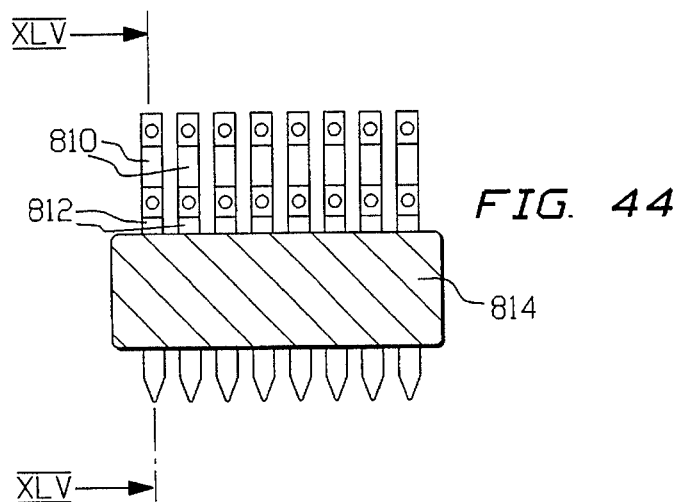
FIG. 44 is a cross-sectional view taken along line XLIV—XLIV in FIG. 43.
Figure 45:
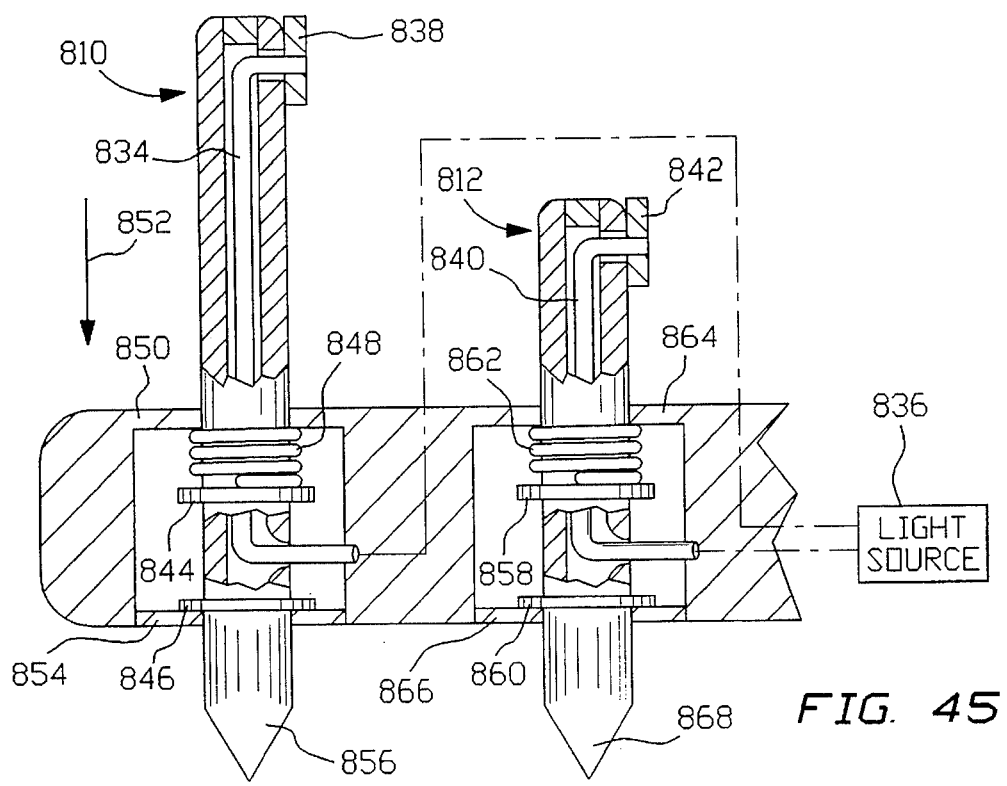
FIG. 45 is a partial cross-sectional view taken along line XLV—XLV in FIG. 44.

It is to be noted that other configurations of the operative components of the device of FIGS. 43–45 are possible and within the scope of the present invention. For example, CCD 826 and its associated circuitry 828 and 830 may be disposed at computer 24 or an intermediate location between the computer and instrument frame 802. In that configuration, optical fiber bundle 824 extends out from instrument frame 802 to the remote CCD. Alternatively, optical fiber bundle 824 may be omitted and CCD 826 positioned in juxtaposition to lens 822.

As depicted in FIGS. 44 and 45, each pin 810 is hollow and contains an end portion of a respective optical fiber 834 extending from a light source 836 inside instrument frame 802 to a mounting bracket 838 at an end of the respective pin 810. Each pin 812 is also hollow and contains an end portion of a respective optical fiber 840 extending from light source 836 to a mounting bracket 842 at an end of the respective pin 812. The distal ends of optical fibers 834 and 840, at mounting brackets 838 and 842, face lens 822, whereby the linear postions of pins 810 and 812 relative to nose portion 814 of instrument frame 802 may be instantaneously and continuously monitored by computer 24 through the video signals received from CCD 826.

As further depicted in FIG. 45, each pin 810 is provided with a pair of spaced perimetrically extending flanges 844 and 846. A helical spring 848 is compressed between a wall 850 of nose portion 814 and flange 844, thereby biasing the respective pin 810 in a direction indicated by an arrow 852. Flange 846 cooperates with another wall 854 of nose portion 814 to limit the distance that a pointed end 856 of the respective pin 810 projects from nose portion 814.

Each pin 812 is provided with a pair of spaced perimetrically extending flanges 858 and 860. A helical spring 862 is compressed between a wall 864 of nose portion 814 and flange 858, thereby biasing the respective pin 812 in a direction indicated by arrow 852. Flange 860 cooperates with another wall 866 of nose portion 814 to limit the distance that a pointed end 868 of the respective pin 812 projects from nose portion 814.

In using the contour data gathering device of FIGS. 43–45, a dental practitioner attaches the instrument frame 802 to pantograph-type component 50 (FIG. 1) via sleeve 806 and set screw 808, thereby fixing the instrument frame and pins 810 and 812 with respect to pantograph arm 56 which is monitored by opto-electrical transducers or video cameras 60 and 62. Pantograph component 50 enables computer 24 to track, from outside the mouth, the translatory motion of an arbitrarily selected reference point on instrument frame 802 inside the mouth of a patient. In addition, described hereinabove, pantograph assembly enables computer 24 to track the orientation of instrument frame 802 inside the patient's mouth. In this manner, computer 24 is continuously informed not only as to the position of the arbitrary reference point, but also the orientation of a coordinate system or reference frame, exemplarily with the reference point as origin.

It is to be noted that other methods for providing computer 24 with data as to the position and orientation of dental instrument 802 are possible. Instead of pantograph assembly, for instance, the encoders and articulated support arm assembly 310 of FIG. 14 may be utilized.

In addition to the data representing the location of an arbitrary reference point on instrument frame 802 inside a patient's mouth and the three-dimensional orientation of the instrument frame, computer 802 is supplied with a data stream from CCD 826 regarding the instantaneous positions of sliding pins 810 and 812. The dental pratitioner presses pointed ends 856 and 868 of pins 810 and 812 against a dental surface and simultaneously draws instrument frame 802 along that surface. During this motion, pins 810 and 812 slide back and forth perpendicularly with respect to nose portion 814 in response to variations (pits and cavities, projections) in the surface of the tooth being scanned. These reciprocating motions tracing a plurality of parallel contours along the tooth surface are sensed by CCD 826 and quantized by computer 24 to form parallel contour data utilizable by conventional CAD/CAM programs previously loaded into computer 24.

The positional tracking of pins 810 and 812 by CCD 826 and computer 24 is facilitated by light output of optical fibers 834 and 840. Computer 24 measures the motions of pins 810 and 812 relative to the arbitrary reference point. Moreover, computer 24 is able to instantaneously correlate the incoming contour data stream(s) with the tooth surface being scanned, owing to the incoming rotational data as to the orientation of instrument frame 802 inside the patient's mouth.

Pairs of pins 810 and 812 are shown as being aligned with one another in FIG. 44. However, contour data is collectible at an enhanced rate if the pins 810 of one row are staggered with the pins 812 of the other row. Such a two-dimensional array of pins 810 and 812 enables a greater pin density, thereby increasing the amount of incoming contour data.

Instrument frame 802 may be provided with a button (not shown) which, when pressed by the dentist, provides computer 24 with a signal that contour data input is commencing.

Figure 46:
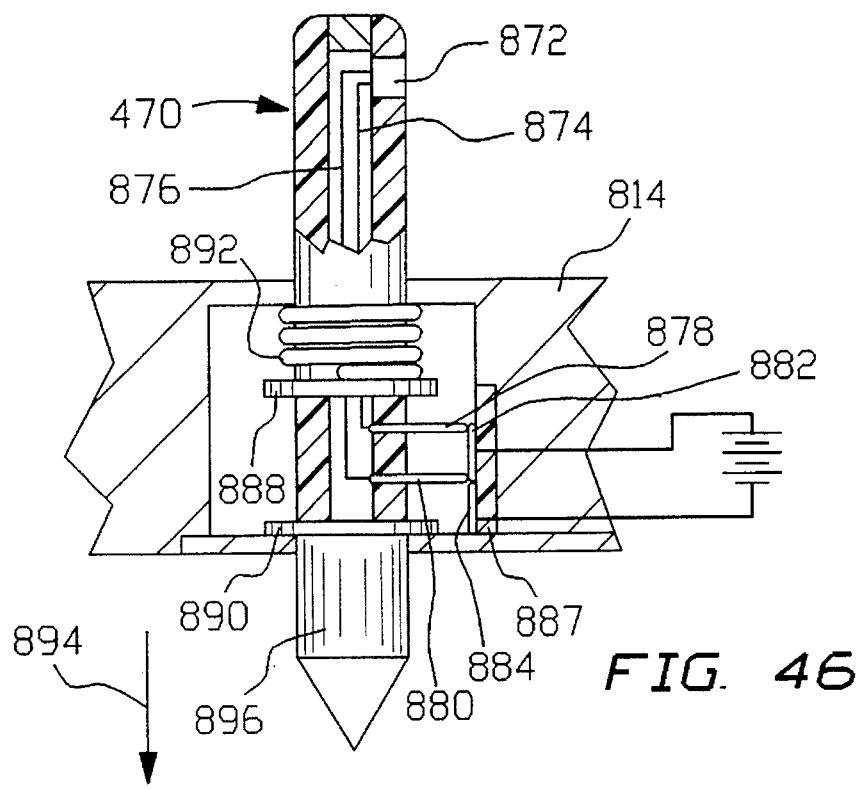
FIG. 46 is a partial cross-sectional view similar to that shown in FIG. 45, showing a modified parallel contour data gathering device in accordance with the present invention.

FIG. 46 depicts another pin or stylus 870 slidably mounted to nose portion 814 of instrument frame 802 in substitution for pins 810 and/or 812. In pin 870, a light-emitting diode 872 forms the light source for facilitating detection by CCD 826 (FIG. 43) and monitoring by computer 24. Diode 872 is connected by a pair of leads 874 and 876 to two brush-type terminals 878 and 880 which are in sliding contact with respective plates 882 and 884. Plates 882 and 884 are connected to opposite terminals of a direct-current voltage source 886 and are insulated from nose portion 814 by a buffer element 487.

As further depicted in FIG. 46, each pin 870 is provided with a pair of spaced perimetrically extending flanges 888 and 890. A helical spring 892 is compressed between wall 850 or 864 (see FIG. 45) of nose portion 814 and flange 888, thereby biasing the respective pin 870 in a direction indicated by an arrow 894. Flange 890 cooperates with wall 854 or 866 of nose portion 814 to limit the distance that a pointed end 896 of the respective pin 870 projects from nose portion 814.

Figure 47:
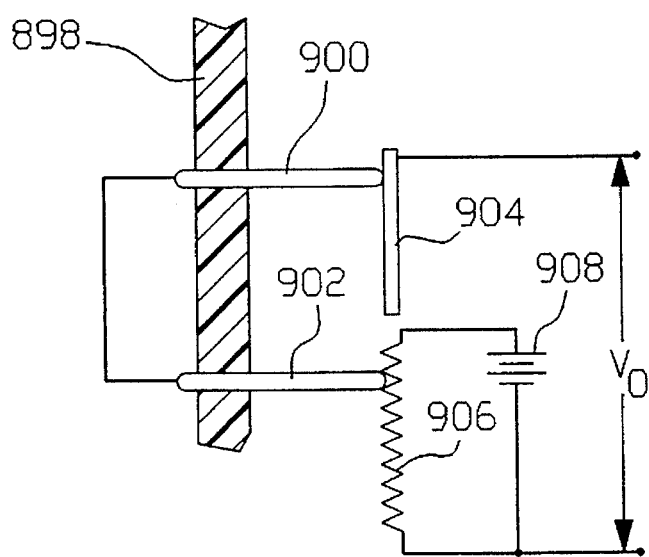
FIG. 47 is a diagram showing a circuit of another parallel contour data gathering device in accordance with the present invention.
Figure 48:
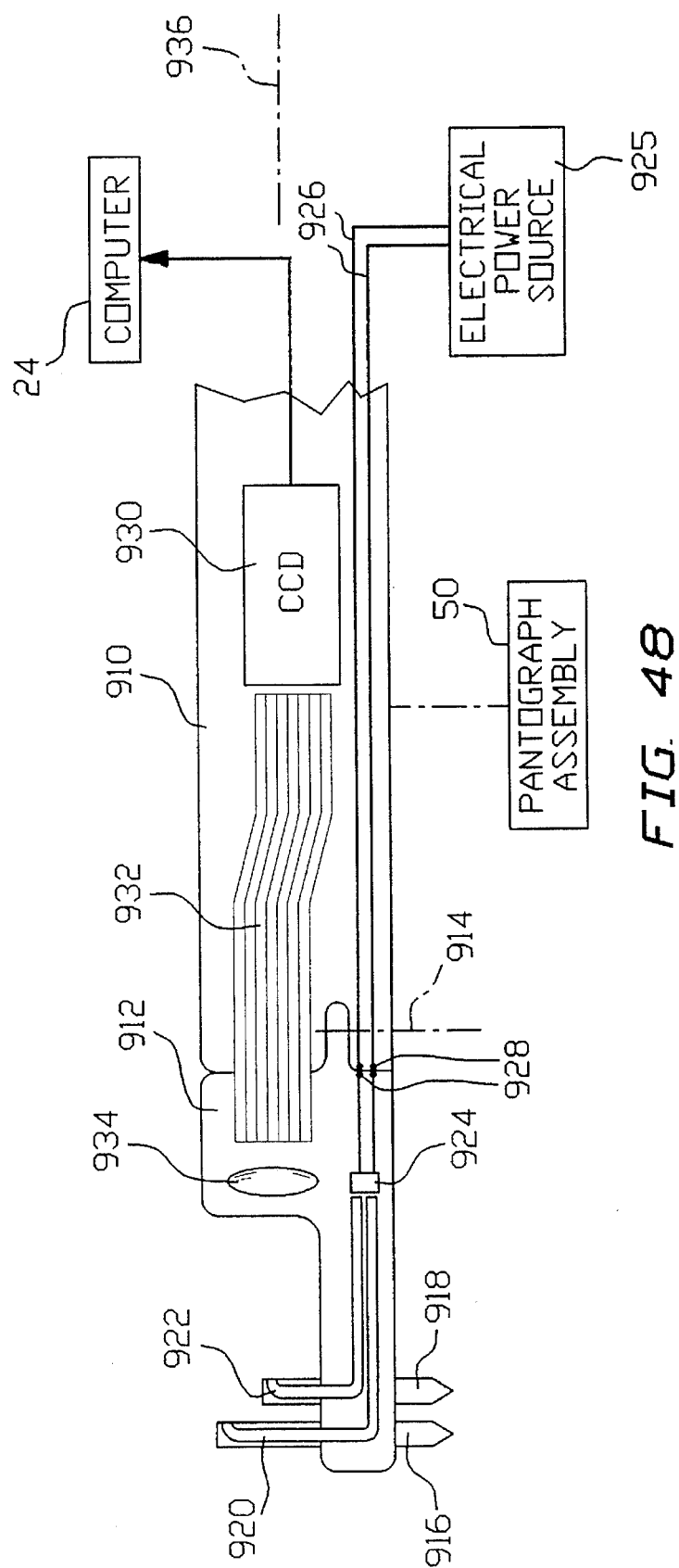
FIG. 48 is a schematic side elevational view of yet another parallel contour data gathering device in accordance with the present invention.

FIG. 47 illustrates a portion of a pin or stylus 898 slidably mounted to a nose portion (e.g. 814 in FIG. 43) of a dental instrument for providing computer 24 (FIG. 1) with digitized data representing a surface contour on a tooth. As described hereinabove with reference to FIGS. 43–45, pin or stylus 898 is one of a plurality of identical stylii all slidably mounted to the nose portion of the instrument frame in a linear or two-dimensional array for providing contour data along a plurality of parallel planes. As further described above with reference to FIGS. 43–45, the dental instrument carrying pins 898 mis removably attachable to pantograph-type component 50 (FIG. 1), whereby computer 24 is also provided with digitzed data representing the location and orientation of a distal end of the dental instrument inside a patient's mouth during use of the dental instrument.

A pair of brush type contacts 900 and 902 are embedded in stylus 898 and operatively engage in a sliding contact a plate 904 and a resistive element 906, respectively. A direct-current voltage source 908 is connected across resistive element 906, while an output voltage $v_0$ is taken across a portion of resistive element 906 depending on the distance that stylus 898 is shifted A reciprocating type motion of pins 916 and 918 which occurs as a dentist moves nose portion 912 along a tooth surface is monitored by computer 24 via digitized video signals arriving from a charge-coupled device ("CCD") and its associated preprocessing circuitry 930. CCD 930 receives optical energy via a bundle of optical fibers 932 extending from a lens 934 in nose portion 912.

The pivoting attachment of nose portion 912 to frame 910 facilitates the collection of parallel contour data by enabling a dentist to orient nose portion at an angle (e.g. a right angle) with respect to a longitudinal axis 936 of instrument frame 910. The angular orientation of nose portion 912 particularly facilitates the collection of parallel contour data along a plurality of parallel planes oriented at the aforementioend angle with respect to axis 936. Computer 24 is able to take the orientation of nose portion 912 into account by monitoring, via pantograph assembly 50, the direction of motion of the distal end of instrument frame 910 during a data gathering motion thereof.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof. angle) with respect to a longitudinal axis 936 of instrument frame 910. The angular orientation of nose portion 912 particularly facilitates the collection of parallel contour data along a plurality of parallel planes oriented at the aforementioned angle with respect to axis 936. Computer 24 is able to take the orientation of nose portion 912 into account by monitoring, via pantograph assembly 50, the direction of motion of the distal end of instrument frame 910 during a data gathering motion thereof.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A method for preparing tooth and tooth restorations, comprising the steps of:

projecting a visible point of light onto a predetermined location on an object, thereby serving as an indicator to an operator that material is to be removed from said object at said location;

guiding a material removal means to said location, upon projection of said visible point of light onto said location; and operating material removal means to remove material from the object at said location.

2. The method recited in claim 1, further comprising the steps of at least partially automatically determining points of excess material on said object and, in a step separate and distinct from said step of projecting, at least partially automatically instructing the operator as to locations of points of excess material on said object.

3. The method recited in claim 2, wherein step of instructing includes the step of displaying visually detectable information.

4. The method recited in claim 3 wherein said step of instructing further includes the step of displaying an image of said object on a display.

5. The method recited in claim 4, further comprising the step of generating electrically encoded data specifying at least surface contours of said object, thereby providing a control unit with information for automatically generating said image.

6. The method recited in claim 5 wherein said step of generating includes the step of optically scanning a surface of said object and transmitting a video signal of said surface to a computer.

7. The system recited in claim 5 wherein said step of generating includes the step of monitoring the location of a tip of a manipulable stylus-type instrument relative to said object and feeding electrically encoded data regarding said location to said computer.

8. The method recited in claim 1, further comprising the step of monitoring the position of said material removal means relative to said object, also comprising the step of terminating projection of said visible point of light upon attainment of a predetermined position by said material removal means.

9. The method recited in claim 1, further comprising the step of monitoring the position of said material removal means relative to said object, also comprising the step of automatically terminating operation of said material removal means upon attainment of a predetermined position by said material removal means.

10. The method recited in claim 1, further comprising the step of monitoring the position of said material removal means relative to said object, also comprising the step of initiating projection of said visible point of light upon attainment of a predetermined position by said material removal means.

11. The method recited in claim 1 wherein said object is a tooth in a patient's mouth.

12. The method recited in claim 1 wherein said object is a dental prosthesis.

13. The method recited in claim 12, further comprising the step of disposing said prosthesis on a holder prior to said step of projecting.

\* \* \* \* \*